United States Patent
Arai et al.

(10) Patent No.: US 11,198,698 B2
(45) Date of Patent: Dec. 14, 2021

(54) ORGANIC SEMICONDUCTOR COMPOSITION, ORGANIC THIN FILM COMPRISING SAME, AND USE THEREOF

(71) Applicants: NATIONAL INSTITUTE OF ADVANCED INDUSTRIAL SCIENCE AND TECHNOLOGY, Tokyo (JP); NIPPON KAYAKU KABUSHIKI KAISHA, Tokyo (JP)

(72) Inventors: Shunto Arai, Tokyo (JP); Tatsuo Hasegawa, Tokyo (JP); Satoru Inoue, Saitama (JP)

(73) Assignees: NATIONAL INSTITUTE OF ADVANCED INDUSTRIAL SCIENCE AND TECHNOLOGY, Tokyo (JP); NIPPON KAYAKU KABUSHIKI KAISHA, Tokyo (JP)

( * ) Notice: Subject to any disclaimer, the term of this patent is extended or adjusted under 35 U.S.C. 154(b) by 75 days.

(21) Appl. No.: 16/080,172

(22) PCT Filed: Feb. 27, 2017

(86) PCT No.: PCT/JP2017/007570
§ 371 (c)(1),
(2) Date: Aug. 27, 2018

(87) PCT Pub. No.: WO2017/150474
PCT Pub. Date: Sep. 8, 2017

(65) Prior Publication Data
US 2019/0048021 A1   Feb. 14, 2019

(30) Foreign Application Priority Data
Feb. 29, 2016   (JP) .............................. JP2016-037213

(51) Int. Cl.
*C07D 495/04*   (2006.01)
*C07D 519/00*   (2006.01)
(Continued)

(52) U.S. Cl.
CPC ......... *C07D 495/04* (2013.01); *C07D 519/00* (2013.01); *H01L 29/786* (2013.01);
(Continued)

(58) Field of Classification Search
CPC ... C07D 495/04; C07D 519/00; H01L 29/786; H01L 29/78603; H01L 51/05; H01L 51/105; H01L 51/0032
See application file for complete search history.

(56) References Cited

U.S. PATENT DOCUMENTS

2013/0062598 A1   3/2013   Usta et al.
2013/0330876 A1   12/2013   Takimiya et al.
(Continued)

FOREIGN PATENT DOCUMENTS

EP   2 077 590 A1   10/2007
EP   2 679 592 A1   1/2014
(Continued)

OTHER PUBLICATIONS

Extended European Search Report in EP Application 17759940.4 dated Jul. 3, 2019.
(Continued)

*Primary Examiner* — Shane Fang
(74) *Attorney, Agent, or Firm* — Greenblum & Bernstein, P.L.C.

(57) ABSTRACT

In the present invention, a composition comprising two types of thienothiophene compounds selected from the group consisting of the compounds indicated by formulas (1) to (4) (in formulas (1) to (4), either one of $R_1$ and $R_2$ represents an alkyl group, an aromatic hydrocarbon group
(Continued)

having an alkyl group or a heterocyclic group having an alkyl group, and the other represents a hydrogen atom, an aromatic hydrocarbon group, a heterocyclic group or a substituent represented by formula (5) (in formula (5), $R_3$ represents an aromatic hydrocarbon group or a heterocyclic group)) can form an organic thin film which is homogeneous over a large area, and an organic semiconductor device including the organic thin film is capable of exhibiting high mobility.

18 Claims, 9 Drawing Sheets

(51) Int. Cl.
    *H01L 51/05*     (2006.01)
    *H01L 29/786*     (2006.01)
    *H01L 51/10*     (2006.01)
    *H01L 51/00*     (2006.01)

(52) U.S. Cl.
    CPC ........ *H01L 29/78603* (2013.01); *H01L 51/05* (2013.01); *H01L 51/105* (2013.01); *H01L 51/0032* (2013.01)

(56) References Cited

U.S. PATENT DOCUMENTS

2015/0228913 A1     8/2015   Miyawaki et al.
2016/0049596 A1*   2/2016   Hanna ................ C09K 19/3491
                                                 257/40

FOREIGN PATENT DOCUMENTS

| EP | 2 894 685 A1 | 7/2015 |
|---|---|---|
| JP | 4581062 B2 | 11/2010 |
| JP | 2012-044109 A | 3/2012 |
| JP | 2014-175392 A | 9/2014 |
| JP | 5615459 B2 | 10/2014 |
| JP | 2014-531435 A | 11/2014 |
| JP | 2015-002342 A | 5/2015 |
| JP | 2015-002342 A1 | 5/2015 |
| JP | 2015-110571 A | 6/2015 |
| JP | 5732595 B2 | 6/2015 |
| WO | 2009/128559 A1 | 10/2009 |
| WO | 2013/039842 A1 | 3/2013 |
| WO | 2014/038708 A1 | 3/2014 |
| WO | 2015/137304 A1 | 9/2015 |

OTHER PUBLICATIONS

S. Inoue et al., "Effects of Substituted Alkyl Chain Length on Solution-Processable Layered Organic Semiconductor Crystals", Chem. Mater., 27, 2015, pp. 3809-3812.
International Search Report issued with respect to Patent Application No. PCT/JP2017/007570, dated May 16, 2017.
International Preliminary Report on Patentability issued with respect to Patent Application No. PCT/JP2017/007570, dated Sep. 4, 2018.

* cited by examiner

[Figure 1]
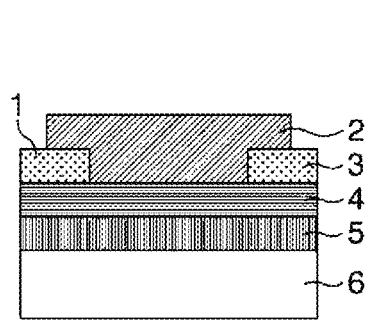
A
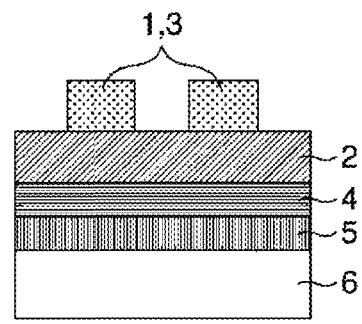
B
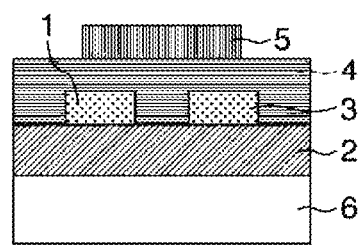
C
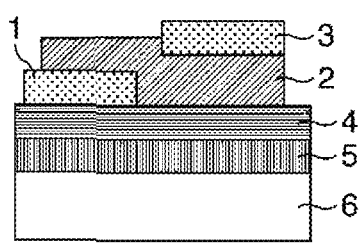
D
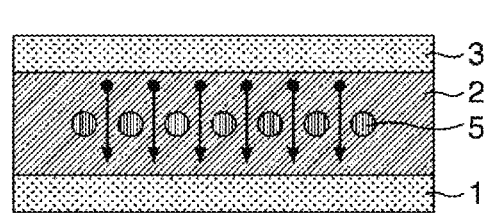
E
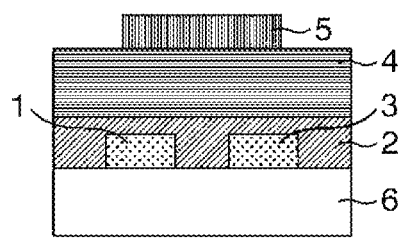
F

[Figure 2]
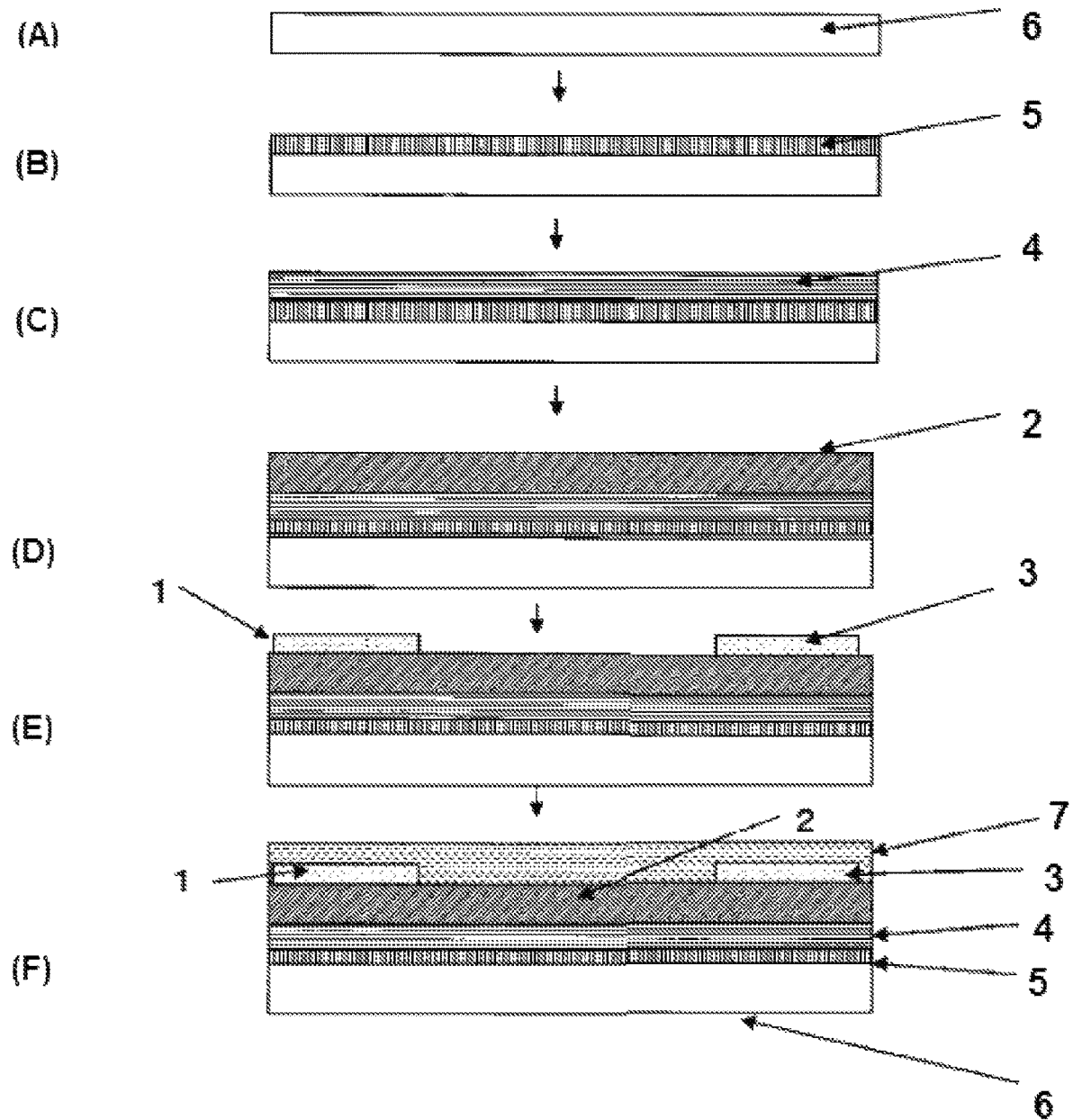

[Figure 3]
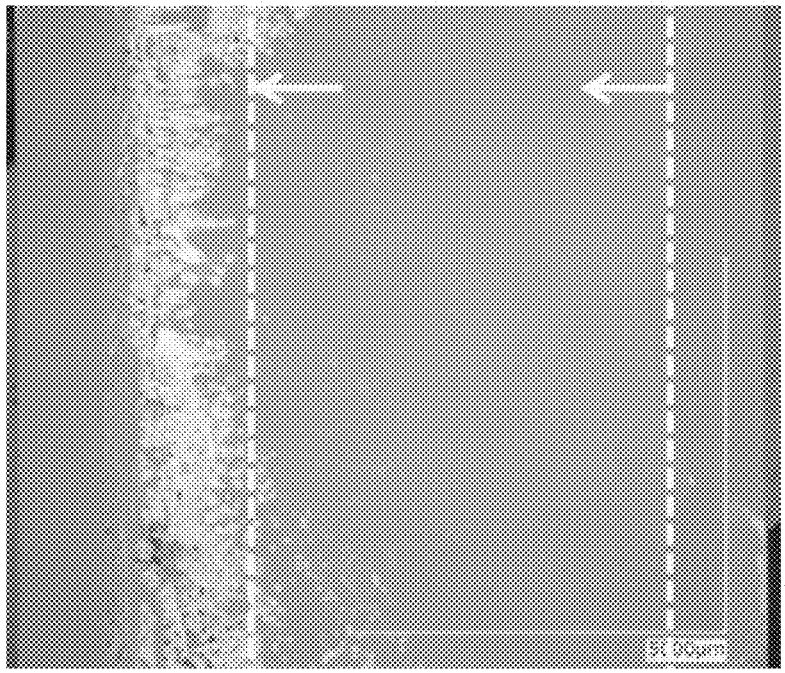
[Figure 4]
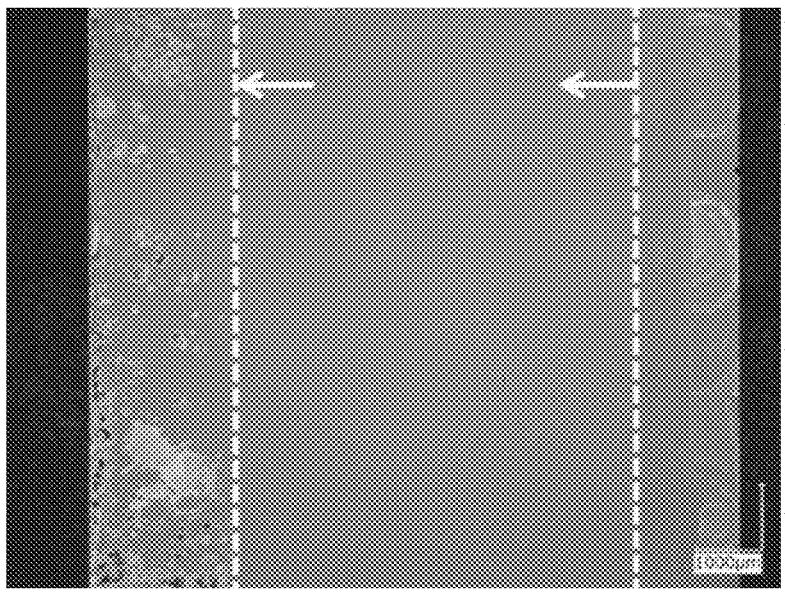

[Figure 5]
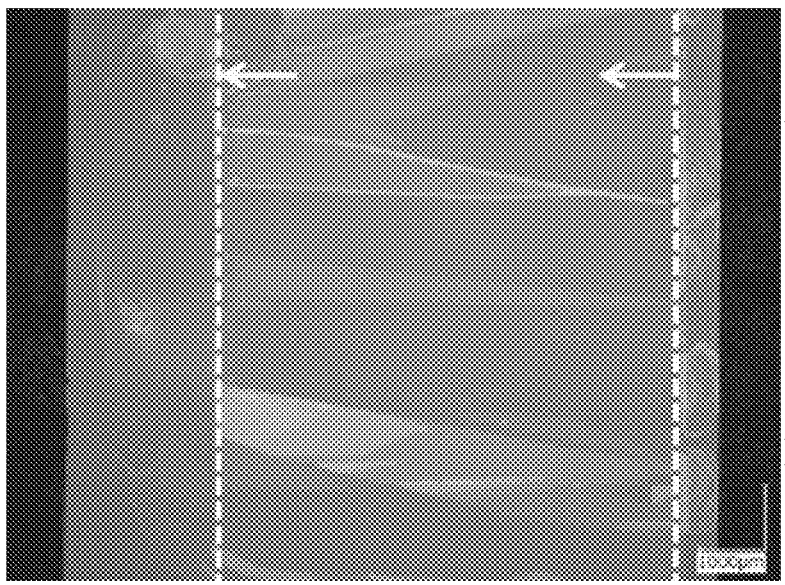
[Figure 6]
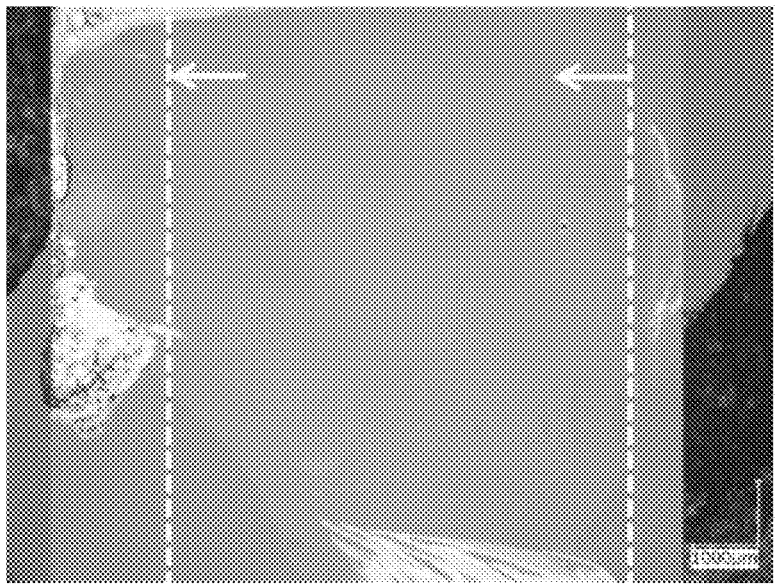

[Figure 7]
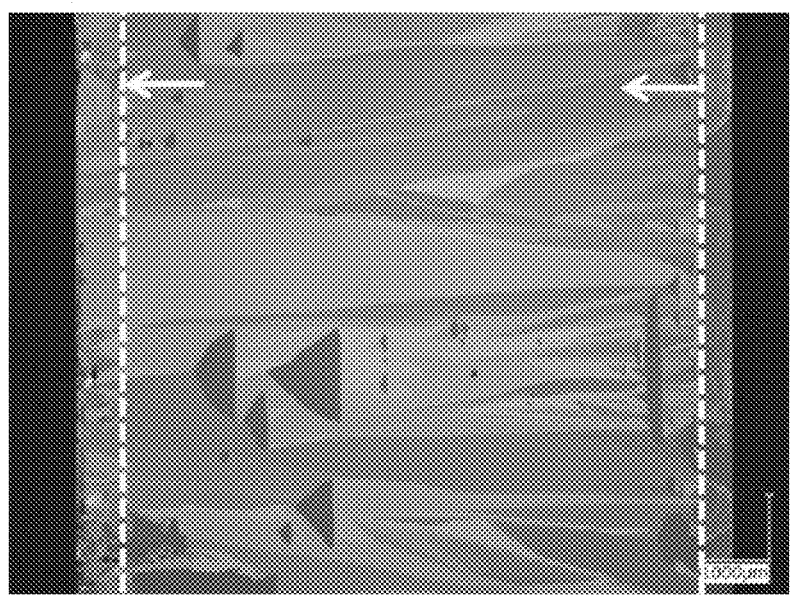
[Figure 8]
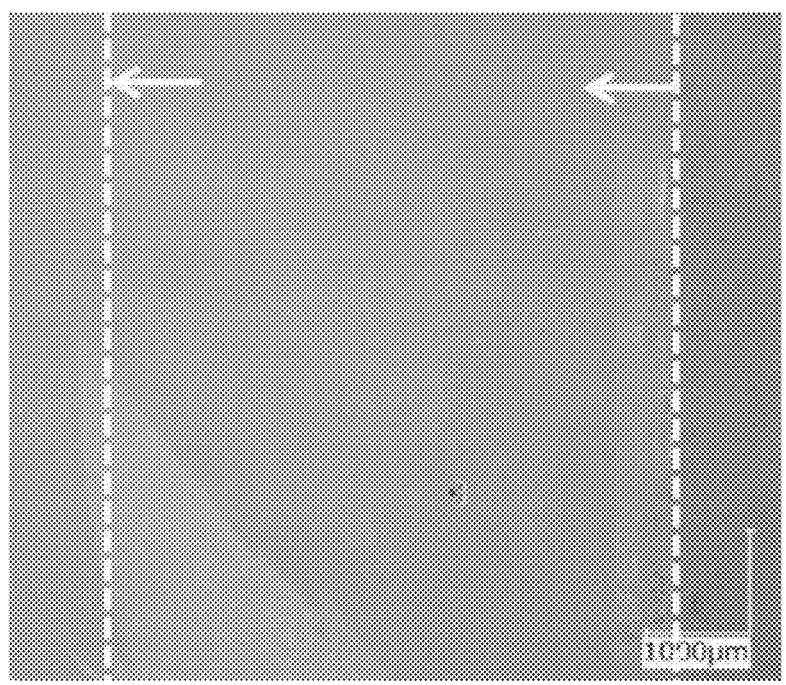

[Figure 9]
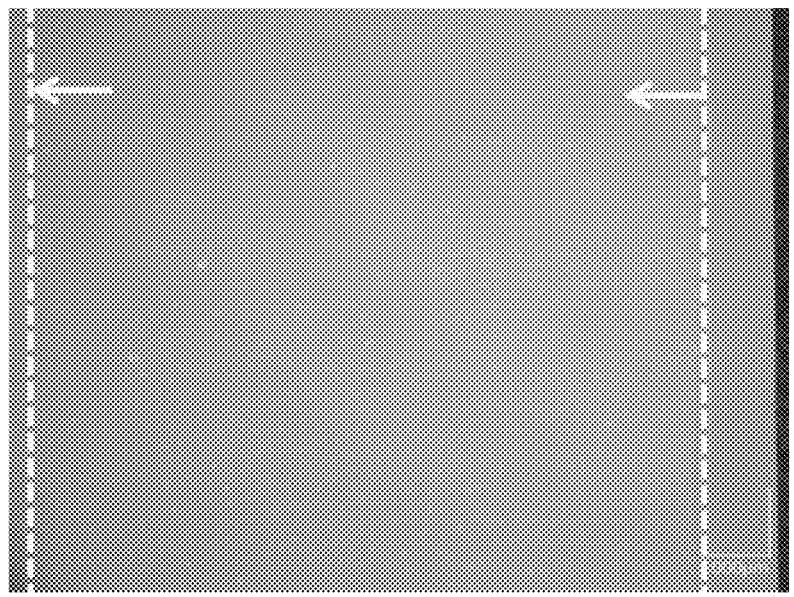
[Figure 10]
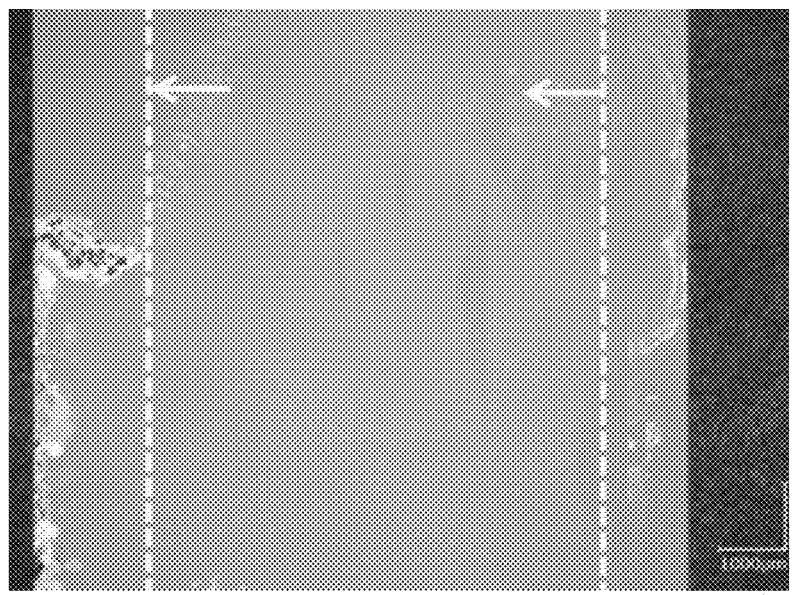

[Figure 11]
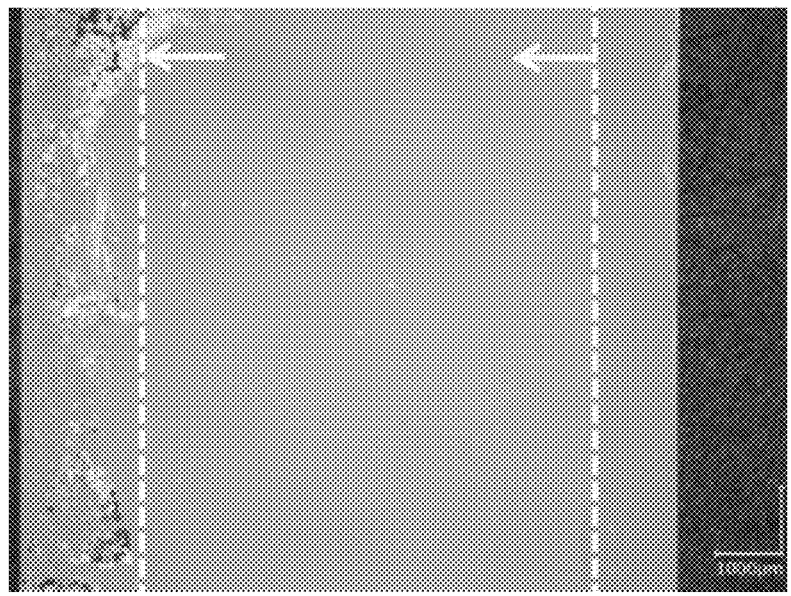
[Figure 12]
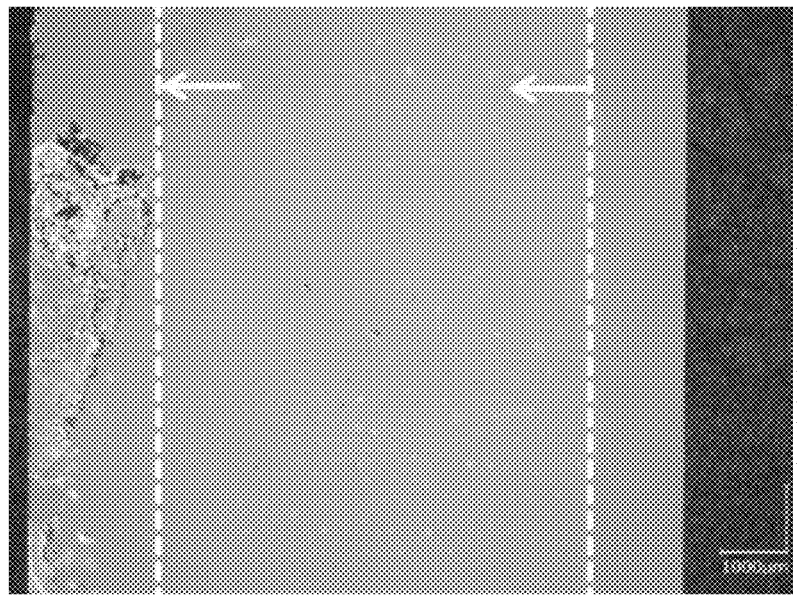

[Figure 13]
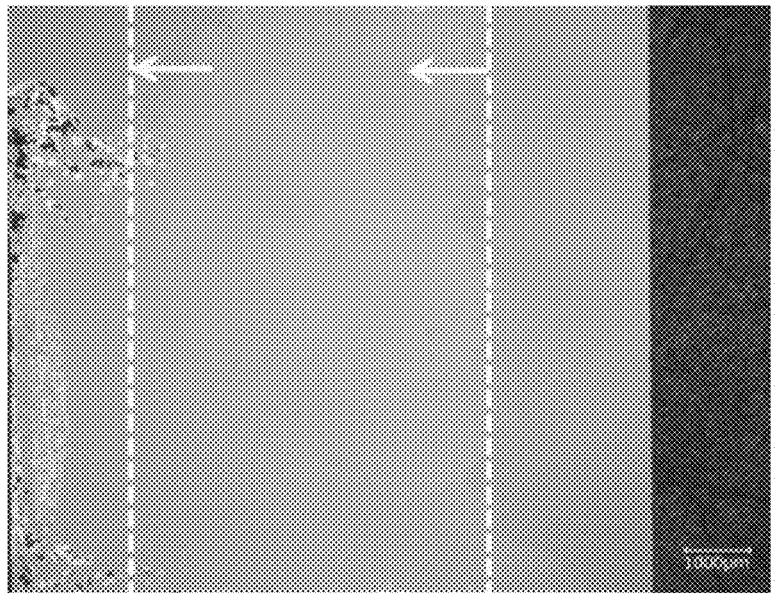
[Figure 14]
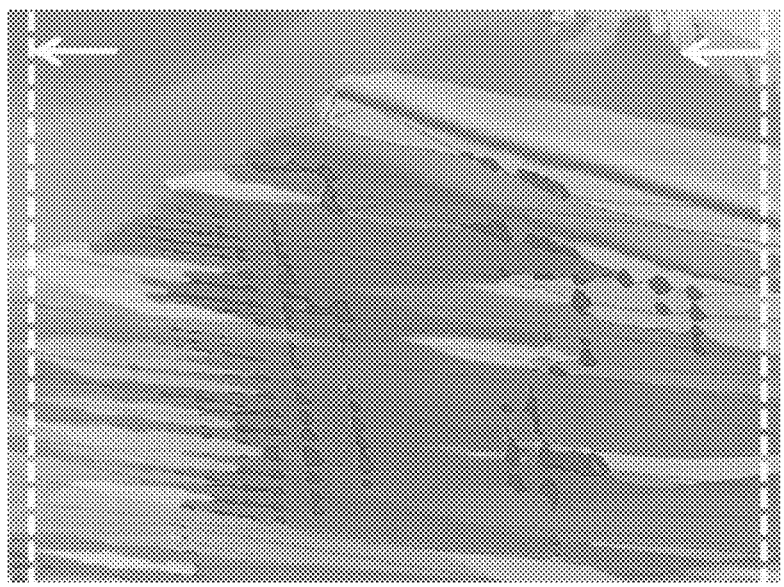

[Figure 15]
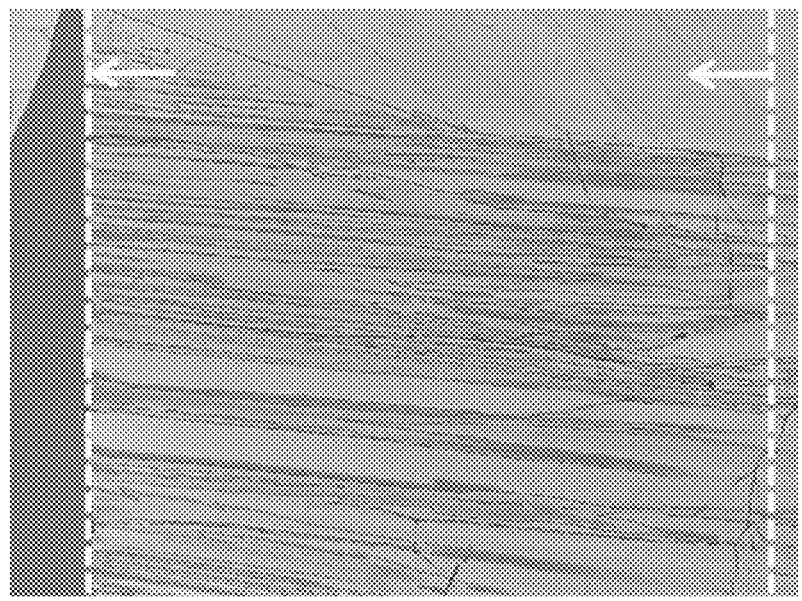

ORGANIC SEMICONDUCTOR COMPOSITION, ORGANIC THIN FILM COMPRISING SAME, AND USE THEREOF

TECHNICAL FIELD

The present invention relates to a composition comprising a plurality of organic semiconductor small molecule compounds, an organic thin film having high homogeneity obtained by using the composition, and an organic semiconductor device including the organic thin film. More particularly, the invention relates to a composition suitable for the formation of the organic thin film that is homogeneous over a large area, which can be used for easy methods such as print and application, etc. Furthermore, the invention relates to an organic semiconductor device using these compositions.

BACKGROUND ART

In recent years, researches and developments about the construction (printed electronics) of an organic semiconductor device using printing techniques are actively performed, because it can make the manufacturing process itself of the device largely efficient, in addition to that it can produce flexible organic semiconductor devices using plastic materials that are not suitable for a manufacturing process requiring a high temperature process.

In such an organic semiconductor device, it is important that a homogeneous organic semiconductor thin film can be formed by the printing technique. Also, for example, in order to apply the organic transistor using an organic semiconductor thin film as a semiconductor layer to a flexible device, it is necessary to form the transistor which can be operated in high speed with low voltage on a flexible substrate. Therefore, characteristics such as high carrier mobility, carrier injection properties to enable low voltage drive, and adaptability to a film formation process at a low temperature are needed for an organic thin film. Besides, suppressing the unevenness of the values of these characteristics is extremely important for obtaining a device which can be used in practical use.

Condensed polycyclic aromatic compounds having a [1]benzothieno [3,2-b] [1] benzothiophene (hereinafter, this is appropriately referred to as "BTBT".) skeleton are known as an organic semiconductor compound having high carrier mobility. Patent Literature 1 discloses BTBT derivatives having formula (x) shown below which are soluble in an organic solvent wherein the derivatives have practical printability and semiconductor characteristics such as the superior carrier mobility. Also, Patent Literature 2 discloses that an improved effect regarding the carrier mobility can be provided by mixing and using these BTBT derivatives in an appropriate combination.

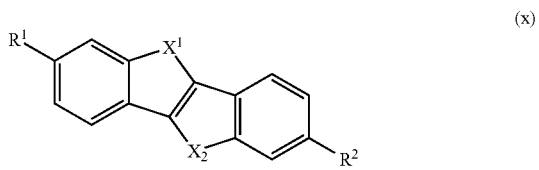

(x)

(In formula (x), $X^1$ and $X^2$ each independently represent a sulfur atom, a selenium atom or a tellurium atom. $R^1$ and $R^2$ each independently represent an unsubstituted or halogen substituted aliphatic hydrocarbon group having a carbon number of 1 to 36.)

Patent Literature 3 and Non-Patent Literature 1 show compounds having specific configurations having charge transport-related molecular unit A including a BTBT frame and unit B as a side chain, and they describe that an organic film having high mobility and performance stability is provided by using these compounds having a highly advanced liquid crystal phase. However, the complicated heat-treatment is necessary at the time of the film formation so that these compounds develop a liquid crystal phase. Besides, they do not describe that the compound of the above specific structure and other organic semiconductor compounds are used as a mixed composition.

Patent Literature 4 discloses that a semiconductor device that has high mobility and small unevenness of the mobility can be developed without a complicated process by using a compound having a structure that an aromatic ring is coupled with a BTBT ring through an acetylene part. The process, however, needs a liquid crystal layer as in Patent Literature 3.

Patent Literature 5 discloses that an organic transistor can be manufactured easily only by typecasting a solution including a compound having a condensation ring with an acetylene part and drying the solution, but Patent Literature 5 just shows the superior solubility of the described compound is connected to the convenience of the process, and there is no specific description relating to a homogeneous film.

That is, Patent Literatures 1 and 2 relate to realization of the high mobility, and Patent Literatures 3 and 4 and Non-Patent Literature 1 relate to the high mobility and reduction of the characteristic unevenness using a complicated heat treatment process. Also, Patent Literature 5 relates to the convenience of the process, but has inarticulate problems of adaptability to specific coating and printing. Therefore, the practical organic semiconductor devices which overcome all technical objects by a simpler and easier method are demanded even now.

CITATION LIST

Patent Literature

Patent Literature 1: Japanese Patent No. 4581062 B
Patent Literature 2: JP2015-002342 A
Patent Literature 3: Japanese Patent No. 5732595 B
Patent Literature 4: Japanese Patent No. 5615459 B
Patent Literature 5: WO2015/137304 A

Non-Patent Literature

Non-Patent Literature 1: S. Inoue et al., Chem. Mater. 2015, 27, 3809-3812.

SUMMARY OF THE INVENTION

Technical Problem

In view of considering the discussed conventional problems, the present invention was completed by findings that an organic thin film which was homogeneous over a large area could be easily formed by using an organic semiconductor composition which contains several types of particular small molecule compounds and that an organic semiconductor device including an organic film obtained by using the organic semiconductor composition provided high mobility and had little characteristic unevenness.

That is, the present invention involves the followings.

(1) A composition comprising two types of thienothiophene compounds selected from the group consisting of compounds represented by formulas (1) to (4):

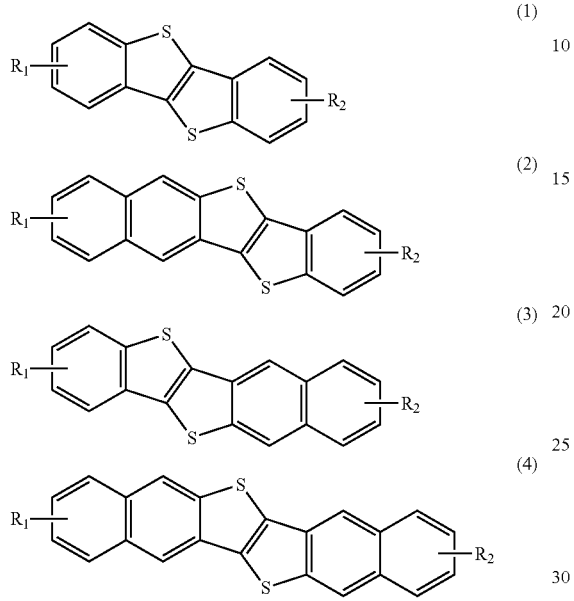

wherein in formulas (1) to (4), either one of $R_1$ and $R_2$ represents an alkyl group, an aromatic hydrocarbon group having an alkyl group or a heterocyclic group having an alkyl group, and the other represents a hydrogen atom, an aromatic hydrocarbon group, a heterocyclic group, or a substituent represented by formula (5):

wherein in formula (5), $R_3$ represents an aromatic hydrocarbon group or a heterocyclic group.

(2) The composition according to (1), wherein the two types of the thienothiophene compounds have different minimum numbers of carbons sequentially bonded through direct bonds between carbon atoms from a terminal carbon atom of $R_1$ to a terminal carbon atom of $R_2$, provided that the terminal carbon atom, when $R_1$ or $R_2$ represents the alkyl group, the aromatic hydrocarbon group having an alkyl group or the heterocyclic group having an alkyl group, is a terminal carbon atom of a main chain of the alkyl group; that the terminal carbon atom, when $R_1$ or $R_2$ represents a hydrogen atom, is a carbon atom at position 6 on a benzothiophene ring or at position 7 on a naphthothiophene ring having the substituent $R_1$ or $R_2$; and that the terminal carbon atom, when $R_1$ or $R_2$ represents the aromatic hydrocarbon group or the heterocyclic group, is a carbon atom on $R_1$ or $R_2$ farthest from a carbon atom which $R_1$ or $R_2$ attaches to, on the benzothiophene ring or the naphthothiophene ring.

(3) The composition according to (2), wherein a difference of the minimum number of carbons sequentially bonded through the direct bonds between carbon atoms from the terminal carbon atom of $R_1$ to the terminal carbon atom of $R_2$ of the two types of the thienothiophene compounds is 2 or more and 18 or less.

(4) The composition according to (3), wherein the difference of the minimum number of carbons sequentially bonded through the direct bonds between carbon atoms from the terminal carbon atom of $R_1$ to the terminal carbon atom of $R_2$ of the two types of the thienothiophene compounds is 2 or more and 12 or less.

(5) The composition according to (1), wherein either one of the two types of the thienothiophene compounds is a thienothiophene compound represented by any one of formulas (6) to (9):

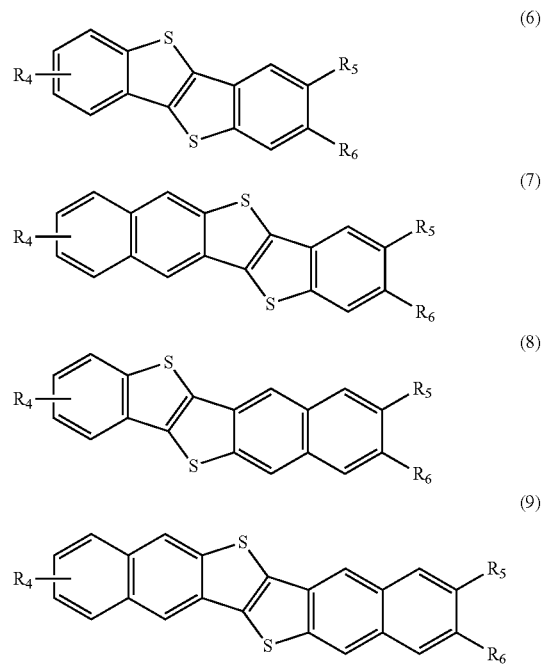

wherein in formulas (6) to (9), $R_4$ represents an alkyl group, an aromatic hydrocarbon group having an alkyl group or a heterocyclic group having an alkyl group, and either one of $R_5$ and $R_6$ represents a hydrogen atom and the other represents an aromatic hydrocarbon group.

(6) The composition according to (5), wherein the both of the two types of the thienothiophene compounds are the thienothiophene compounds represented by the any one of formulas (6) to (9).

(7) The composition according to (1), comprising the two types of the thienothiophene compounds having different carbon numbers of a main chain of the alkyl group in the alkyl group, the aromatic hydrocarbon group having an alkyl group or the heterocyclic group having an alkyl group which either one of the substituent $R_1$ or $R_2$ represents,
wherein the content ratio of the thienothiophene compound having a main chain having a larger carbon number is 1 mass % or more and 90 mass % or less.

(8) The composition according to (7), comprising the two types of the thienothiophene compounds, wherein a difference of the carbon number of the main chain of the alkyl group in the alkyl group, the aromatic hydrocarbon group having an alkyl group or the heterocyclic group having an alkyl group which either one of the substituent $R_1$ or $R_2$ represents is 2 or more and 8 or less.

(9) The composition according to (1), wherein at least one of the two types of the thienothiophene compounds is a thienothiophene compound represented by formulas (10) to (13):

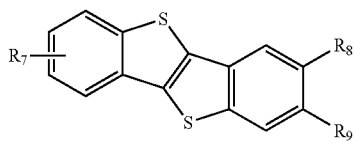
(10)

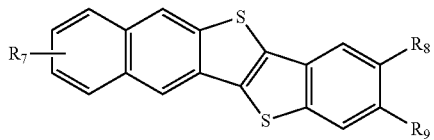
(11)

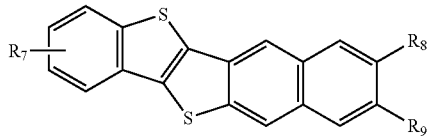
(12)

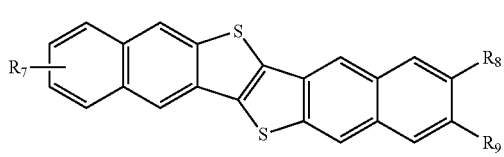
(13)

wherein in formulas (10) to (13), $R_7$ represents an alkyl group, an aromatic hydrocarbon group having an alkyl group and a heterocyclic group having an alkyl group, either one of $R_8$ and $R_9$ represents a hydrogen atom, and the other represents a substituent group represented by formula (5).

(10) The composition according to (1), wherein either one of the two types of the thieonothiophene compounds is a thieonothiophene compound represented by formulas (6) to (9):

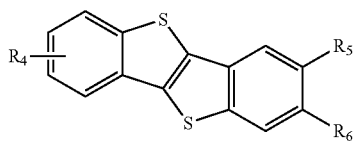
(6)

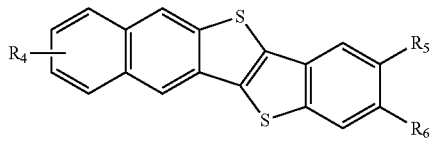
(7)

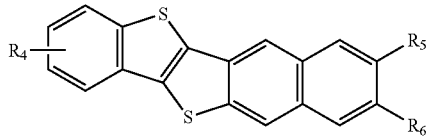
(8)

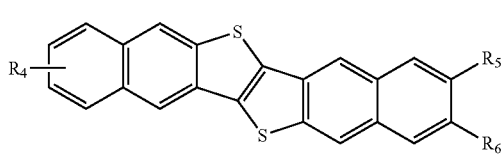
(9)

wherein in formulas (6) to (9), $R_4$ represents an alkyl group, an aromatic hydrocarbon group having an alkyl group or a heterocyclic group having an alkyl group, either one of $R_5$ and $R_6$ represents a hydrogen atom, and the other represents an aromatic hydrocarbon group, and the other is a thienothiophene compound represented by any one of formulas (10) to (13):

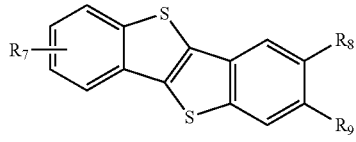
(10)

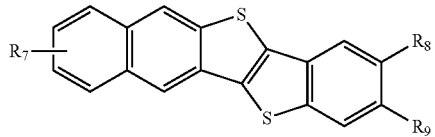
(11)

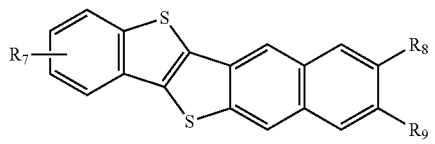
(12)

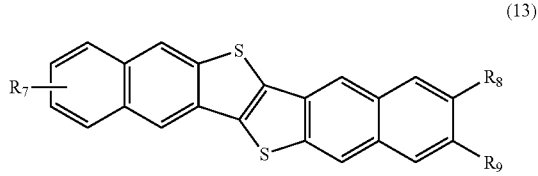
(13)

wherein, in formulas (10) to (13), $R_7$ represents an alkyl group, an aromatic hydrocarbon group having an alkyl group and a heterocyclic group having an alkyl group, either one of $R_8$ and $R_9$ represents a hydrogen atom, and the other represents a substituent group represented by formula (5).

(11) The composition according to (10), wherein a content of the thienothiophene compound represented by any one of formulas (10) to (13) to a total mass of the two types of the thienothiophene compounds is from 5 to 40 mass %.

(12) An organic thin film formation material comprising the composition according to any one of (1) to (11) and an organic solvent.

(13) An organic thin film obtained by using the organic thin film formation material according to (12).

(14) The organic thin film according to (13), having a thickness of 4 nm or more and 30 nm or less.

(15) A method for producing an organic thin film comprising:
applying or printing the organic thin film formation material according to (12) to a substrate, and
removing the organic solvent from the organic thin film formation material applied or printed to the substrate.

(16) An organic semiconductor device comprising the organic thin film according to (13) or (14).

(17) The organic semiconductor device according to (16), wherein the organic semiconductor device is an organic thin film transistor.

Effect of the Invention

By using a composition containing at least two types of thienothiophene compounds having specific structures, an organic thin film which is homogeneous over a large area can be formed without needing a complicated process. Also, the organic semiconductor device having high homogeneity, which can balance the high carrier mobility and the improvement of the carrier injection efficiency, can be provided by using the organic thin film.

BRIEF DESCRIPTION OF DRAWINGS

FIG. 1 shows a schematic cross-section indicating some embodiment examples of the organic thin film transistors of the present invention, (a) is a schematic cross-section indicating the embodiment example of the bottom gate-bottom contact type organic thin film transistor, (b) is a schematic cross-section indicating the embodiment example of the bottom gate-top contact type organic thin film transistor, (c) is a schematic cross-section indicating the embodiment example of the top gate-top contact type organic thin film transistor, (d) is a schematic cross-section indicating the embodiment example of the bottom gate-top and bottom contact type organic thin film transistor, (e) is a schematic cross-section indicating the embodiment example of the electrostatic induction transistor, and (f) is a schematic cross-section indicating the embodiment example of the top gate-bottom contact type organic thin film transistor.

FIG. 2 shows an illustration to describe the production method of the bottom gate-top contact type organic thin film transistor as an embodiment example of the organic thin film transistor of the present invention, and (a) to (f) are schematic cross-sections indicating each steps of the above production methods.

FIG. 3 shows the polarizing micrograph which shows the organic thin film of Example 1.

FIG. 4 shows the polarizing micrograph which shows the organic thin film of Example 2.

FIG. 5 shows the polarizing micrograph which shows the organic thin film of Example 3.

FIG. 6 shows the polarizing micrograph which shows the organic thin film of Example 4.

FIG. 7 shows the polarizing micrograph which shows the organic thin film of Example 5.

FIG. 8 shows the polarizing micrograph which shows the organic thin film of Example 6.

FIG. 9 shows the polarizing micrograph which shows the organic thin film of Example 7.

FIG. 10 shows the polarizing micrograph which shows the organic thin film of Example 8.

FIG. 11 shows the polarizing micrograph which shows the organic thin film of Example 9.

FIG. 12 shows the polarizing micrograph which shows the organic thin film of Example 10.

FIG. 13 shows the polarizing micrograph which shows the organic thin film of Example 11.

FIG. 14 shows the polarizing micrograph which shows the organic thin film of Comparative Example 1.

FIG. 15 shows the polarizing micrograph which shows the organic thin film of Comparative Example 2.

FORM TO CARRY OUT INVENTION

Hereinafter, the present invention is explained in detail.
The composition of the present invention contains two types of thienothiophene compounds selected from the group consisting of compounds represented by the above formulas (1) to (4).

In formulas (1) to (4), either one of $R_1$ or $R_2$ represents an alkyl group, an aromatic hydrocarbon group having an alkyl group or a heterocyclic group having an alkyl group, and the other represents a hydrogen atom, an aromatic hydrocarbon group, a heterocyclic group or a substituent represented by formula (5). In formula (5), $R_3$ represents an aromatic hydrocarbon group or a heterocyclic group.

The compounds represented by formulas (1) to (4) can be synthesized in reference to the above-mentioned prior literature.

The alkyl group which $R_1$ or $R_2$ in formulas (1) to (4) represents is a linear, branched or cyclic alkyl group, and the alkyl group having a carbon number of 1 to 30 is desirable. Specific examples of the alkyl group include methyl group, ethyl group, n-propyl group, n-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, iso-propyl group, iso-butyl group, t-butyl group, iso-pentyl group, t-pentyl group, sec-pentyl group, iso-hexyl group, sec-heptyl group, sec-nonyl group, 2-ethylhexyl group, 3-ethylheptyl group, 4-ethyloctyl group, 2-butyloctyl group, 3-butylnonyl group, 4-butyldecyl group, 2-hexyldecyl group, 3-octylundecyl group, 4-octyldodecyl group, 2-octyldodecyl group, 2-decyltetradecyl group, cyclohexyl group, cyclopentyl group, adamantyl group and norbornyl group.

The alkyl group that $R_1$ or $R_2$ in formulas (1) to (4) represents is more preferably a straight or branched alkyl group such as n-butyl group, n-hexyl group, n-octyl group, n-decyl group, n-dodecyl group, 2-ethylhexyl group, 3-ethylhexyl group, 3-ethyloctyl group or 3-butyloctyl group, and further preferably, n-hexyl group, n-octyl group or n-decyl group.

As an aromatic hydrocarbon group in the aromatic hydrocarbon group having an alkyl group which $R_1$ or $R_2$ of formulas (1) to (4) represents, an aromatic hydrocarbon group having a carbon number of 6 to 24 is preferable, as a specific example, phenyl group, biphenyl group, naphthyl group, anthryl group, phenanthryl group, pyrenyl group and fluorenyl group are included. Phenyl group or naphthyl group is desirable.

Specific examples of the alkyl group in the aromatic hydrocarbon group having an alkyl group which $R_1$ or $R_2$ in formulas (1) to (4) represents are the same as the specific examples of the alkyl group which $R_1$ or $R_2$ of formulas (1) to (4) represents, and the examples of the preferably alkyl group are also the same.

Note that the number of the alkyl group in the aromatic hydrocarbon group having an alkyl groups which $R_1$ or $R_2$ of formula (1) to (4) represents may be a plural number, and the aromatic hydrocarbon group may also have a substituent except for the alkyl group.

As an aromatic hydrocarbon group having an alkyl group which $R_1$ or $R_2$ in formulas (1) to (4) represents, a phenyl group having an alkyl group or a naphthyl group having an alkyl group is preferable, a phenyl group having an alkyl group on position p or position m, or a naphthyl group having an alkyl group on position 4 or position 6 are more preferable, and a phenyl group having an alkyl group on position p or position m is further preferable.

As a heterocyclic group in the heterocyclic group having an alkyl group which $R_1$ or $R_2$ in formulas (1) to (4) represents, a heterocyclic group having a carbon number of 5 to 15 is preferable, and the specific examples include furanyl group, thienyl group, benzofuranyl group, benzothienyl group, pyridyl group, bipyridyl group, quinolyl group, pyrazyl group, thienothiophenyl group and pyrazolyl group. Thienyl group, benzothienyl group or thieno thiophenyl group is desirable.

Specific examples of the alkyl group in the heterocyclic group having an alkyl group which $R_1$ or $R_2$ in formulas (1) to (4) represents are the same as the specific examples of the alkyl group which $R_1$ or $R_2$ of formulas (1) to (4) represents, and the examples of the preferably alkyl group are also the same.

Note that the number of the alkyl group in the heterocyclic group having an alkyl group which $R_1$ or $R_2$ of formulas (1) to (4) represents may be a plural number, and the heterocyclic group may also have a substituent except for the alkyl group.

Examples of the aromatic hydrocarbon group which $R_1$ or $R_2$ in formulas (1) to (4) represents are the same as the examples of the aromatic hydrocarbon group in the aromatic hydrocarbon group having an alkyl group which $R_1$ or $R_2$ of formulas (1) to (4) represents, and examples of the preferred aromatic hydrocarbon group are also the same.

Examples of the heterocyclic group which $R_1$ or $R_2$ of formulas (1) to (4) represents are the same as the examples of the heterocyclic group in the heterocyclic group having an alkyl group which $R_1$ or $R_2$ of formulas (1) to (4) represents, and examples of the preferred heterocyclic group are also the same.

Examples of the aromatic hydrocarbon groups which $R_3$ in formula (5) represents are the same as the aromatic hydrocarbon group in the aromatic hydrocarbon group having an alkyl group which $R_1$ or $R_2$ of formulas (1) to (4) represents, and examples of the preferred aromatic hydrocarbon are the same.

Examples of the heterocyclic groups which $R_3$ in formula (5) represents are the same as the heterocyclic group in the heterocyclic group having an alkyl group which $R_1$ or $R_2$ of formulas (1) to (4) represents, and examples of the preferred heterocyclic group are also the same.

As $R_1$ and $R_2$ in formulas (1) to (4), when one of $R_1$ and $R_2$ is an alkyl group, the other is preferably an aromatic hydrocarbon group, a heterocyclic group or a substituent represented by formula (5), the other is more preferably an aromatic hydrocarbon group or a substituent represented by formula (5). When one of $R_1$ and $R_2$ is an aromatic hydrocarbon group having an alkyl group or a heterocyclic group having an alkyl group, the other is preferably a hydrogen atom or a substituent represented by formula (5), the other is more preferably a hydrogen atom.

The composition of the present invention preferably contains the two types of thienothiophene compounds having different minimum numbers of carbons sequentially bonded through direct bonds between carbon atoms from a terminal carbon atom of $R_1$ to a terminal carbon atom of $R_2$. Note that the terminal carbon atom, when $R_1$ or $R_2$ represents the alkyl group, the aromatic hydrocarbon group having an alkyl group or the heterocyclic group having an alkyl group, means a terminal carbon atom of a main chain of the alkyl group; that the terminal carbon atom, when $R_1$ or $R_2$ represents a hydrogen atom, means a carbon atom at position 6 on a benzothiophene or at position 7 on a naphtothiophene having the substituent $R_1$ or $R_2$; and that the terminal carbon atom, when $R_1$ or $R_2$ represents the aromatic hydrocarbon group or the heterocyclic group, means a carbon atom on $R_1$ or $R_2$ farthest from a carbon atom which $R_1$ or $R_2$ attaches to, on the benzothiophene ring or the naphtothiophene ring.

More specifically for examples, in the compound represented by formula (21):

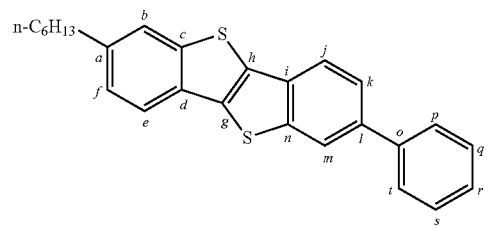

(21)

wherein in formula (21), a to t in formula (21) represent a position of a carbon atom on the aromatic hydrocarbon ring and the heterocyclic ring.

One of the terminal carbon atoms is the terminal carbon atom of the hexyl group which is the main chain of alkyl group, the other is the carbon atom r in the phenyl group, which is the farthest from the carbon atom 1 which the phenyl group attaches to in the partial structure in the benzothiophene. The minimum number of carbon atoms sequentially bonded through direct bonds in the both of the terminal carbon atoms is 20 which is a total of 6 of the hexyl group and carbons a, b, c, d, g, h, i, j, k, l, o, p, q and r.

Explains are conducted by using another example. In the compound represented by formula (22):

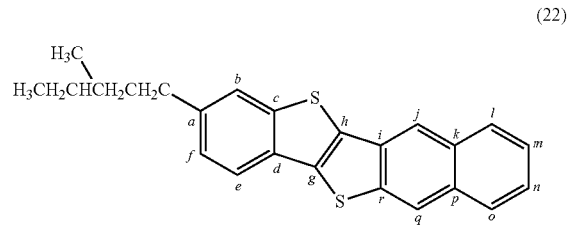

(22)

wherein in formula (22), a to r represent a position of a carbon atom on the aromatic hydrocarbon ring and the heterocyclic ring.

One of the terminal carbon atoms is the terminal carbon atom of the pentyl group which is the main chain of alkyl group, the other is the carbon atom of position 7 (carbon n) in the partial structure of the naphtothiophene. The minimum number of carbon atoms sequentially bonded through direct bonds in the both of the terminal carbon atoms is 17 which is a total of 5 of the pentyl group and carbons a, b, c, d, g, h, i, j, k, l, m, and n.

Explains are performed by using further another example. In the compound represented by formula (23):

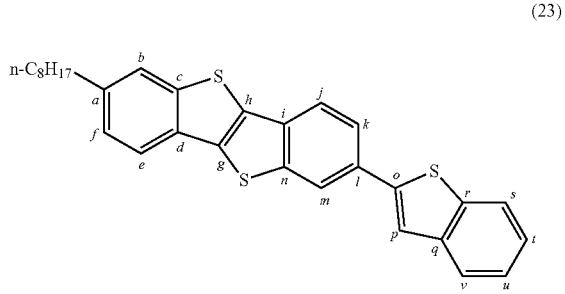

(23)

wherein in formula (23), a to v represent a position of a carbon atom on the aromatic hydrocarbon ring and the heterocyclic ring.

One of the terminal carbon atoms is the terminal carbon atom of the n-octyl group which is the main chain of alkyl group, the other is the carbon atoms t and u. The minimum number of carbon atoms sequentially bonded through direct bonds from the terminal carbon atom of the n-octyl group to the carbon atom t is 24 which is a total of 8 of the octyl group and carbons a, b, c, d, g, h, i, j, k, l, o, p, q, r, s and t. On the other hand, the minimum number of carbon atoms sequentially bonded through direct bonds from the terminal carbon atom of the n-octyl group to the carbon atom u is 23 which is a total of 8 of the octyl group and carbons a, b, c, d, g, h, i, j, k, l, o, p, q, v and u. Therefore, the minimum number of carbon atoms sequentially bonded through direct bonds from the terminal carbon atom of $R_1$ to the terminal carbon atom of $R_2$ of the compound represented by formula (23) is 23.

The difference of the minimum number of carbon atoms sequentially bonded through direct bonds from the terminal carbon atom of $R_1$ to the terminal carbon atom of $R_2$ of the two types of the thienothiophene compounds contained in the composition of the present invention is not particularly limited to, but in view of the solubility of these compounds, the difference of the minimum number is preferably 2 or more and 18 or less, more preferably 2 or more and 12 or less, further preferably 2 or more and 8 or less, and especially preferably 4 or more and 6 or less.

It is preferred that one of the thienothiophene compounds contained in the composition of the present invention is a thienothiophene compound represented by any one of the above described formulas (6) to (9), and it is more preferred that the other is also a thienothiophene compound represented by any one of formulas (6) to (9).

In formulas (6) to (9), $R_4$ represents the same meaning as $R_1$ in formulas (1) to (4) and preferred one of $R_4$ represents the same meaning as preferred one of $R_1$ in formula (1). The alkyl group, the alkyl group of the aromatic hydrocarbon group having an alkyl group, or the alkyl group of the heterocyclic group having an alkyl group represented by substituent $R_4$ is preferably linear, and $R_4$ is more preferably a linear alkyl group.

In formulas (6) to (9), either one of $R_5$ and $R_6$ represents a hydrogen atom, the other represents an aromatic hydrocarbon group. The specific examples and the preferred one of the aromatic hydrocarbon group are same as the aromatic hydrocarbon groups represented by $R_2$ in formula (1) to (4).

In formulas (6) to (9), the substituent position of $R_4$ is not limited, but when $R_5$ is a hydrogen atom, the substitution position of the substituent $R_4$ is preferably position 6 in the partial structure of the benzothiophene ring which $R_4$ attaches to, or position 7 in the naphotothiophene ring which $R_4$ attaches to. When $R_6$ is a hydrogen atom, the substitution position of the substituent $R_4$ is preferably position 5 in the partial structure of the benzothiophene ring which $R_1$ attaches to, or position 6 in the naphotothiophene ring which $R_4$ attaches to.

When both of the two types of the thienothiophene compounds contained in the composition of the present invention are the thienothiophene compounds represented by formulas (6) to (9), the composition preferably contains two types of thienothiophene compounds having different carbon numbers of the main chain of the alkyl group in the alkyl group, the aromatic hydrocarbon group having an alkyl group or the heterocyclic group having an alkyl group represented by the substituent $R_4$. The difference of the carbon numbers of the main chain of the alkyl group in the alkyl group, the aromatic hydrocarbon group having an alkyl group or the heterocyclic group having an alkyl group represented by the substituent $R_4$ of the two types of the thienothiophene compounds is preferably 2 or more and 8 or less. Note that the content ratio of the two types of the thienothiophene compounds having different carbon numbers of the main chain of the alkyl group in the alkyl group, the aromatic hydrocarbon group having an alkyl group or the heterocyclic group having an alkyl group represented by the substituent $R_4$ is not particularly limited to, but the content ratio of the compound having the larger carbon number of the main chain of the alkyl group in the two types of the thienothiophene compounds to the total content of the two types of the thienothiophene compounds is preferably 1 mass % or more and 90 mass % or less, more preferably 3 mass % or more and 70 mass % or less, further preferably 3 mass % or more and 60 mass % or less, and most preferably 3 mass % or more and 50 mass % or less.

At least one of the thienothiophene compounds contained in the composition of the present invention is also preferably a thienothiophene compound represented by any one of formulas (10) to (13).

In formulas (10) to (13), $R_7$ represents the same meaning as $R_1$ in formulas (1) to (4). The preferred one of $R_7$ is also the same as the preferred one of $R_1$ in formula (1). The alkyl group in the alkyl group, the aromatic hydrocarbon group having an alkyl group or the heterocyclic group having an alkyl group which the substituent $R_4$ represents is preferably linear, $R_7$ represents more preferably a linear alkyl group.

In formulas (10) to (13), either one of $R_8$ or $R_9$ represents hydrogen atom, the other represents a substituent represented by formula (5). The specific examples and preferred one of $R_3$ in the substituent represented in formula (5) are same as the specific examples and preferred one of $R_3$ in the substituent represented by formula (5) which $R_1$ or $R_2$ in formula (1) represents.

In formulas (10) to (13), the substituent position of $R_7$ is not limited to, but when $R_9$ is a hydrogen atom, the substitution position of the substituent $R_7$ is preferably position 5 in the partial structure of the benzothiophene ring which $R_7$ attaches to, or position 6 in the naphotothiophene ring which $R_7$ attaches to. When $R_9$ is a hydrogen atom, the substitution position of the substituent $R_7$ is preferably position 6 in the partial structure of the benzothiophene ring which $R_4$ attaches to, or position 7 in the naphotothiophene ring which $R_4$ attaches to.

When one of the thienothiophene compounds contained in the composition of the present invention is a thienothiophene compound represented by formulas (10) to (13), the embodiment that the other is a compound represented by formulas (6) to (9) is preferred. When the compound represented by any one of formulas (6) to (9) and the compound represented by formulas (10) to (13) are used together, the content ratios of the two types of the thienothiophene compounds are not particularly limited, but the thienothiophene compound represented by formulas (6) to (9) is preferably contained excessively. More specifically, to the total mass of the two type of thienothiophene compounds, the content of the thienothiophene compound represented in formulas (10) to (13) is preferably less than 50 mass %, more preferably from 5 to 40 mass %. The minimum of carbon number sequentially bonded by the direct bonds from the terminal carbon atom of $R_1$ to the terminal carbon atom of $R_2$ in the thienothiophene compounds represented by any one of formulas (6) to (9) and the minimum of carbon number sequentially bonded by the direct bonds from the terminal carbon atom of $R_1$ to the terminal carbon atom of R$_2$ in the thienothiophene compounds represented by any one of formulas (10) to (13) are preferably different, and more preferably the minimum of carbon number sequentially bonded by the direct bonds from the terminal carbon atom of R$_1$ to the terminal carbon atom of R$_2$ in the thienothiophene compounds represented by any one of formulas (6) to (9) is smaller than the minimum of carbon number sequentially bonded by the direct bonds from the terminal carbon atom of R$_1$ to the terminal carbon atom of R$_2$ in the thienothiophene compounds represented by any one of formulas (10) to (13).

Although the specific examples of the thienothiophene compounds represented by any of formulas (1) to (4) contained in the composition of the present invention is shown, the thienothiophene compounds used in the present invention are not limited thereto. Note that the number indicated in the brackets behind the number of the exemplary specific compound described below means the minimum of carbon number sequentially bonded by the direct bonds from the terminal carbon atom of R$_1$ to the terminal carbon atom of R$_2$ in the each compound.

No.1(20)

No.2(22)

No.3(24)

No.4(24)

-continued

No.5(28)
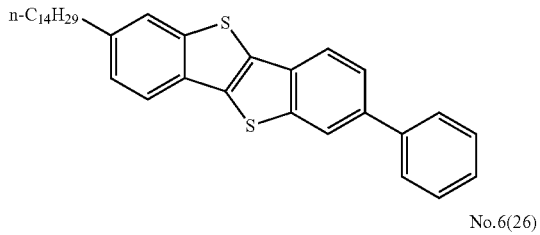

No.6(26)
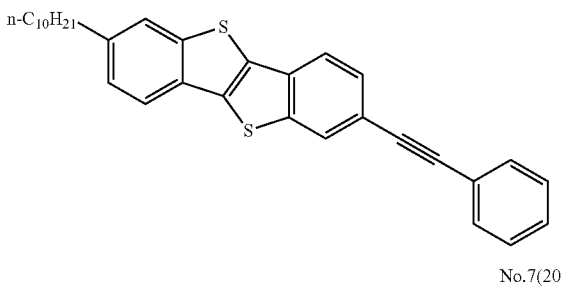

No.7(20)
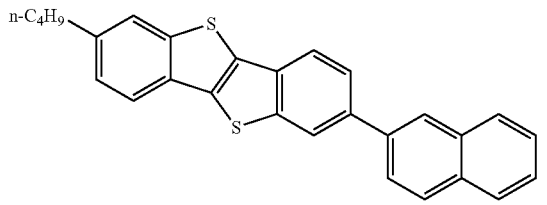

No.8(28)
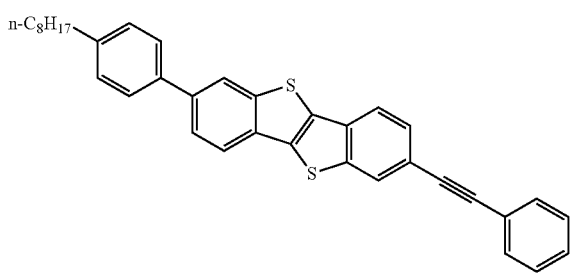

No.9(23)
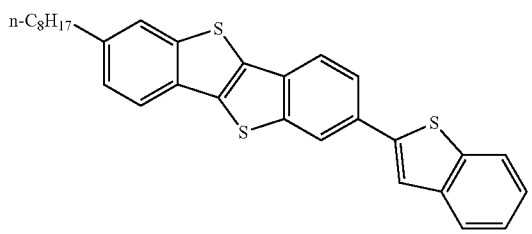

No.10(22)
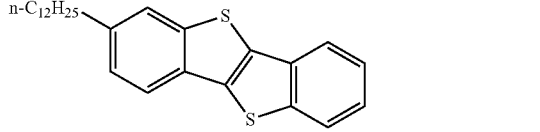

No.11(20)
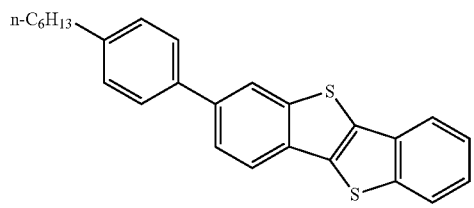

No.12(24)
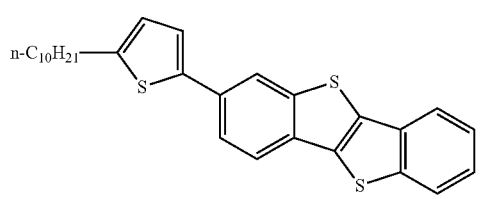

No.13(24)
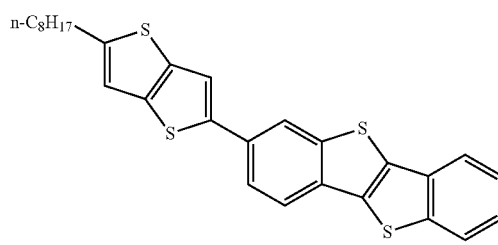

No.14(20)
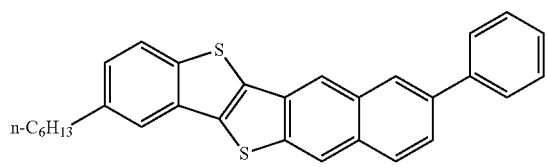

No.15(22)
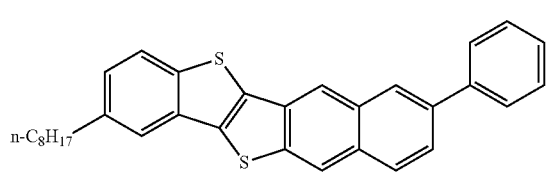

No.16(24)
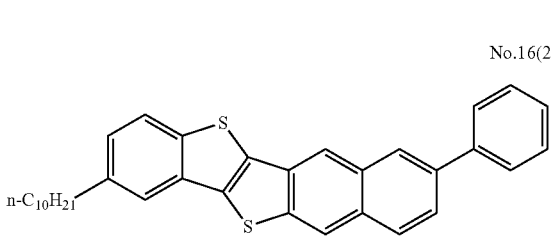

No.17(20)
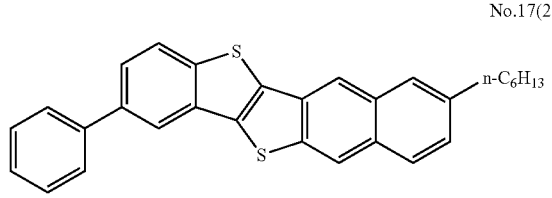

No.18(22)
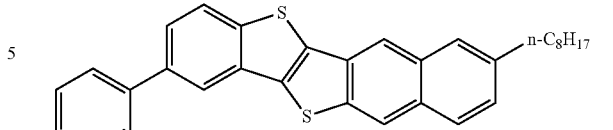

No.19(22)
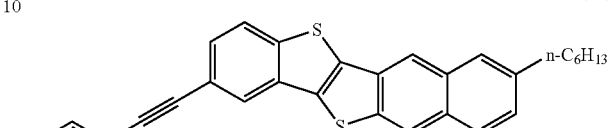

No.20(24)
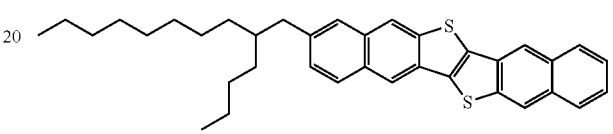

No.21(20)
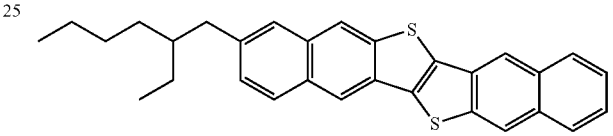

No.22(18)
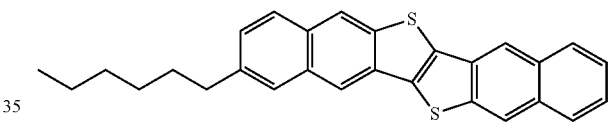

No.23(30)
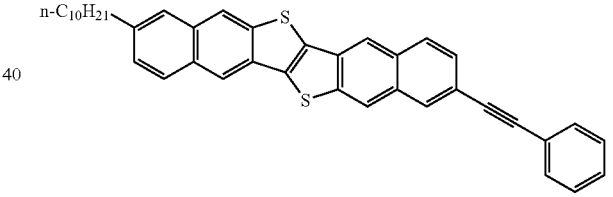

Then, the organic thin film formation material containing the composition of the present invention and an organic solvent for forming an organic thin film by the applying and printing method is explained. The organic thin film formation material can be produced by dissolving the composition of the present invention in an organic solvent. It is preferable to completely dissolve the composition in the organic solvent. The usable solvent is not particularly limited as long as the solvent can dissolve the composition of the present invention to form a film on a substrate. The solvent can be used singularly or in combination of multiple solvents as a mixture.

As an organic solvent, halogens such as dichloromethane, chloroform, dichloroethane, chlorobenzene, and dichlorobenzene; ethers such as diethyl ether, tetrahydrofuran, anisole and phenetole; ketone such as acetone, methyl ethyl ketone, methyl isobutyl ketone, cyclopentanone and cyclohexanone; amides such as dimethylacetamide, dimethylformamide, N-methylpyrrolidone; alcohols such as methanol, ethanol, isopropanol and butanol; fluoro alcohols such as fluorinated alcohols such as octafluoropentanol and pentafluoropentanol; esters such as ethyl acetate, butyl acetate, ethyl benzoate, butyl benzoate and diethyl carbonate; aromatic hydrocarbons such as benzene, toluene, xylene, mesitylene, ethyl benzene, tetrahydronaphthalene and cyclohexylbenzene; hydrocarbons such as hexane, cyclohexane, octane, decane and decahydronaphthalene can be used.

When the practical applying and printing method is considered, the safety and the storing of solvent, and the composition stability in the manufacturing conditions are needed to be taken into account. Preferably, at least one of the solvents having a boiling point of 150° C. or higher, and more preferably, at least one of the solvents having a boiling point of 180° C. or higher.

In the organic thin film formation material, the total concentration of the compounds represented by formula (1) to the solvents is 0.01 mass % to 10 mass % and is preferably 0.05 mass % to 5 mass %. Furthermore, the concentration can be appropriately selected by depending on the types of the solvents, the thickness of the formed thin film, the formation methods of the thin film and so on.

In the organic thin film formation material of the present invention, in order to improve the characteristics of the field-effect transistor and impart other characteristics, other organic semiconductor materials, polymer materials and additives may be mixed as requested, as far as the effects of the present invention are not interfered. Examples of the additives include a carrier agent, a conducting material, a viscosity modifier, a surface tension modifier, a leveling agent, a penetrant, a rheology modifier, an orientation agent and a dispersant.

The organic thin film can be formed from the organic thin film formation material by using various applying and printing methods. That is, by applying or printing the organic thin film formation material of the present invention on a substrate and then removing the organic solvent from the organic thin film formation material applied or printed on the substrate, the organic thin film can be formed. It is preferred that the organic thin film used in an organic semiconductor device has no defect in a large area and is homogeneous and excellent in reproductivity. The thickness of the organic thin film is, depending on the applications thereof, usually 1 nm to 300 nm, preferably 3 nm to 50 nm, and more preferably 4 nm to 30 nm.

Although various applying and printing methods can be used as a method for forming an organic thin film, an appropriate method may be selected in view of the viscosity of the organic thin film formation material, the desired thickness of film, the pattern shape and so on. Specific examples include a spin coating method, a drop casting method, a dip coating method, a bar coating method, a blade coating method, a slit coating method, a dye coating method, a spray method, a relief printing method such as a flexographic printing method and a resin relief printing, a planographic printing methods such as an offset lithography method, a dry offset lithography method and a pad printing method, an intaglio printing method such as a gravure printing method, a stencil printing method such as a silk-screen printing method, a mimeograph printing method and a lithographic printing method, an ink jet printing method, a microcontact printing method, and a method where the two or more methods described above are combined. In view of the ease of the process and the device, the method for forming the organic thin film may be preferably used under the atmosphere pressure and the ambient temperature. After that, by removing the residual solvent by natural drying and thermal drying, etc., from the organic thin film formation material on the substrate, the organic thin film may be formed. A material capable of forming a homogeneous organic thin film under such conditions is needed. By using the organic thin film formation material of the present invention, a good thin film can be obtained.

An organic semiconductor device can be manufactured by using the organic thin film provided from the two types of the thienothiophene compounds represented by formulas (1) to (4). As an example of the organic semiconductor device, an organic transistor is described in detail.

An organic transistor has two electrodes (a source electrode and a drain electrode) in contact with an organic semiconductor and controls the current flowing between the electrodes by means of a voltage applied to another electrode called a gate electrode.

Generally, in an organic transistor device, a structure in which a gate electrode is insulated with an insulating film (Metal-Insulator-Semiconductor MIS structure) is often used. A structure in which a metal oxide film is used as an insulating film is called an MOS structure. In addition, a structure in which a gate electrode is formed via a shot key barrier (that is, an MES structure) is available, but the MIS structure is often used for an organic transistor.

Hereinafter, the organic transistor is explained below in detail using drawings, but the present invention is not limited to these structures. FIG. 1 shows some embodiment examples of the organic transistor device.

In each embodiment example shown in FIG. 1, reference numeral 1 denotes a source electrode, reference numeral 2 denotes a semiconductor layer obtained by using the composition of the present invention, reference numeral 3 denotes a drain electrode, reference numeral 4 denotes an insulator layer, reference numeral 5 denotes a gate electrode, and reference numeral 6 denotes a substrate, respectively. It should be noted that the arrangement of each layer and electrode can be appropriately selected depending on the applications of the device. A to D, and F, in which the current flows in a direction parallel to the substrate, are called a lateral transistor. A is called a bottom-contact and bottom gate structure, and B is called a top contact and bottom gate structure. Also, C is provided with a source electrode and a drain electrode as well as an insulator layer on a semiconductor, and additionally forms a gate electrode thereon, being called a top-contact and top-gate structure. D has a structure called a top and bottom-contact and bottom-gate transistor. F is a bottom-contact and top-gate structure. E is a schematic diagram of a transistor having a longitudinal structure, or a static induction transistor (SIT). This SIT spreads the current flow in a plane to enable a large number of carriers to be moved at a time. Also, since the distance between the electrodes can be reduced due to the longitudinal arrangement of the source electrode and the drain electrode, the response is fast. Thus, the SIT can be preferably used in applications for allowing a large amount of current to flow and for switching at high speed. It should be noted that, although a substrate is not drawn in E of FIG. 1, a substrate is usually provided external of the source or drain electrode represented by reference numerals 1 and 3 in E of FIG. 1.

Each component in each embodiment example is described.

It is necessary for the substrate 6 to hold each layer to be formed thereon without delaminating. The substrate 6 can be fabricated from insulating materials such as resin plates or films, paper, glass, quartz, and ceramics; by forming an insulating layer on a conductive substrate material such as metals and alloys using coating and the like, or from combinations of materials such as resins and inorganic materials. Examples of the resin films include polyethylene terephthalate, polyethylene naphthalate, polyether sulfone, polyamide, polyimide, polycarbonate, cellulose triacetate, and polyetherimide. Use of resin films and paper can provide flexible and light-weight devices and enhances the practical utility. The thickness of the substrate is usually 1 µm to 10 mm and preferably 5 µm to 5 mm.

In the source electrode 1, the drain electrode 3, and the gate electrode 5, materials having electrical conductivity are used. For example, metals such as platinum, gold, silver, aluminum, chromium, tungsten, tantalum, nickel, cobalt, copper, iron, lead, tin, titanium, indium, palladium, molybdenum, magnesium, calcium, barium, lithium, potassium, and sodium and alloys containing thereof; conductive oxides such as $InO_2$, $ZnO_2$, $SnO_2$, and ITO; conductive polymer compounds such as polyaniline, polypyrrole, polythiophene, polyacetylene, polyparaphenylenevinylene, and polydiacetylene; semiconductors such as silicon, germanium, and gallium arsenide; carbon materials such as carbon black, fullerenes, carbon nanotubes, graphite, and graphene can be used. Also, the conductive polymer compounds and semiconductors may be doped. Examples of a dopant include inorganic acid such as hydrochloric acid and sulfuric acid; organic acids having an acidic functional group such as sulfonic acid; Lewis acids such as $PF_5$, $AsF_5$, and $FeCl_3$; halogen atoms such as iodine; and metal atoms such as lithium, sodium, and potassium. Boron, phosphorous, arsenic, and the like are also frequently used as a dopant for inorganic semiconductors such as silicon.

Also, conductive composite materials obtained by dispersing carbon black, metal particles, and the like in the above-described dopants are used. In order to reduce the contact resistance of the source electrode 1 and the drain electrode 3, which are to be in direct contact with the semiconductor, it is important to select an appropriate work function or to treat surfaces.

Also, the distance between the source electrode and the drain electrode (the channel length) is a key factor to determine the characteristics of the device. The channel length is usually 0.01 to 300 m and preferably 0.1 to 100 µm. The shorter the channel length, the larger the amount of current can be obtained. However, in contrast, short channel effects such as influences from contact resistance are caused, making control difficult. Thus, a proper channel length is required. The width between the source electrode and the drain electrode (the channel width) is usually 10 to 10000 µm and preferably 100 to 5000 µm. Also, it is possible to form a channel having a larger width by allowing the electrodes to have a comb-like structure and the like. Depending on the amount of current required, the structure of the device and the like, it is necessary to adjust the width to an appropriate length. Each structure (shape) of the source electrode and the drain electrode is described. Each structure of the source electrode and the drain electrode may be the same or different.

In the case of the bottom-contact structure, each electrode is fabricated generally by using a lithography method, and also each electrode is preferably formed into a rectangle. Printing precision in various printing methods has been enhanced recently, and precise fabrication of electrodes by using techniques such as inkjet printing, gravure printing, or screen printing has been enabled. In the case of the top contact structure in which electrodes are mounted on a semiconductor, deposition can be made using a shadow mask and the like. Direct printing and formation of electrode patterns has been also enabled by using techniques such as inkjet. The length of the electrodes is the same as the aforementioned channel width. The width of the electrodes is, although not particularly specified, preferably smaller in order to reduce the area of the device to the extent that the electric characteristics can be stabilized. The width of the electrodes is usually 0.1 to 1000 µm and preferably 0.5 to 100 µm. The thickness of the electrode is usually 0.1 to 1000 nm, preferably 1 to 500 nm, and more preferably 5 to 200 nm. The electrodes 1, 3 and 5 are each connected with wiring, which is fabricated of substantially the same material as the electrodes.

As the insulator layer 4, materials having insulation characteristics are used. Examples of the material that may be used include polymers such as polyparaxylylene, polyacrylate, polymethyl methacrylate, polystyrene, polyvinyl phenol, polyamide, polyimide, polycarbonate, polyester, polyvinyl alcohol, polyvinyl acetate, polyurethane, polysulfone, fluorine resins, epoxy resins, and phenol resins and copolymers by combination of these; metal oxides such as silicon dioxide, aluminum oxide, titanium oxide, and tantalum oxide; ferroelectric metal oxides such as $SrTiO_3$ and $BaTiO_3$; dielectrics, such as nitrides such as silicon nitride and aluminum nitride, sulfides, and fluorides; or polymers in which particles of these dielectrics are dispersed. This insulator layer preferably has high electrical insulation characteristics in order to reduce leak current. This can decrease the film thickness thereby to increase the insulation capacity, increasing the amount of current to be obtained. Also, to enhance the mobility in a semiconductor, it is preferred that the surface energy on the surface of the insulator layer is decreased and that the film is smooth without asperities. Thus, in some cases, a self-assembled monolayer and a double insulator layer may be formed. The film thickness of the insulator layer 4 is, although depending on materials, usually 0.1 nm to 100 µm, preferably 0.5 nm to 50 µm, and more preferably 1 nm to 10 µm.

The compositions of the present invention can be used as a material of the semiconductor layer 2. The organic thin film formation material obtained by dissolving the compositions in a solution is formed into the organic thin film of the present invention by using the aforementioned applying and printing method as the semiconductor layer 2.

In the extent that necessary functions are exhibited, the thinner the thickness of the semiconductor layer 2 is the more preferable it is. The thickness is usually 1 nm to 300 nm, preferably 3 nm to 50 nm, and more preferably 4 nm to 30 nm. By satisfying the above range of the thickness, the semiconductor layer 2 which is homogeneous over a large area can be easily formed.

On an organic transistor, other layer can be provided, for example, between the substrate layer and the insulating film layer, between the insulating film layer and the semiconductor layer, or on the exterior of the device, as required. For example, formation of a protective layer directly or via other layer on the organic semiconductor layer can diminish outside atmosphere influences such as humidity. Also, the formation of the protective layer has advantages to stabilize electric characteristics such as an ability to increase the ON/OFF ratio of the organic transistor device.

As the protective layer described above, although not particularly limited, for example, films made from various resins such as epoxy resins, acrylic resins such as polymethyl methacrylate, polyurethane, polyimide, polyvinyl alcohol, fluorine resins, and polyolefins; inorganic oxide films such as silicon oxide, aluminum oxide, and silicon nitride; and films made of dielectrics such as nitride films are preferably used. Particularly, resins (polymers) having a small permeability of oxygen and moisture and a small water-absorbing ratio. Gas-barrier protective materials developed for organic EL displays can be used. The film thickness of the protective layer is, although any film thickness can be selected depending on the purpose, usually 100 nm to 1 mm.

Also, preliminary surface modifications or surface treatments are performed on a substrate or an insulator layer on which an organic semiconductor layer is to be stacked, enabling the characteristics as an organic transistor device to be improved. Adjustment of the degree of hydrophilicity/hydrophobicity of the substrate surface, for example, can improve the quality of a film to be deposited on the substrate and the film deposition ability. Particularly, organic semiconductor materials may largely change in the characteristics depending on the film conditions such as molecular orientation. Thus, it is conceivable that surface treatments to the substrate, the insulator layer, and the like, control molecular orientation in the interface portion between the substrate and an organic semiconductor layer subsequently to be deposited or reduce trap sites on the substrate and the insulator layer, to improve the characteristics such as carrier mobility.

A trap site refers to a functional group, such as a hydroxyl group, which is present on an untreated substrate. If such functional groups are present, electrons are attracted to the functional group, and, as the result, the carrier mobility is decreased. Accordingly, decreases in trap sites may be often effective for improving characteristics such as carrier mobility.

Examples of the surface treatment to improve characteristics as above described include self-assembled monolayer treatments with hexamethyldisilazane, octyltrichlorosilane, and octadecyltrichlorosilane; surface treatments with polymers; acid treatments with hydrochloric acid, sulfuric acid, and acetic acid; alkaline treatment with sodium hydroxide, potassium hydroxide, calcium hydroxide, and ammonia; ozone treatments; fluorination treatment; plasma treatments with oxygen and argon; treatments for forming Langmuir-Blodgett films; treatments for forming thin films of other insulators and semiconductors; mechanical treatments; electric treatments such as corona discharge; and rubbing treatments by use of fibers; and combinations thereof.

In the present invention, as a method for forming each layer except for the semiconductor layer 2, vacuum evaporation method, sputtering method, applying method, printing method, sol-gel method, or the like can be appropriately used. In view of the productivity, applying method or ink jet printing method is preferable.

Generally, the performance characteristics of a field-effect transistor are determined by carrier mobility of a semiconductor layer, conductivity, capacitance of an insulation layer, an element configuration (electrode distance and width between a source and a drain and film thickness of an insulation layer, etc.), and the like. For the organic material used for a semiconductor layer of the field-effect transistor, a high carrier mobility, a homogeneous characteristic and a carrier injection characteristic are required. Furthermore, it is also required that the organic thin film which is to be a semiconductor layer can be formed by a simple and easy method. The organic thin film of the present invention has the characteristics required in the semiconductor layer and can provide the production of a device which is lightweight, excellent in flexibility and durable without any complicated heating step. The device can be used as a switching device of an active matrix of a display, etc.

The organic transistor is also used as a digital device or an analogue device such as a memory circuit device, a signal driver circuit device and a signal processing circuit device. By the combinations thereof, a display, an IC card and an IC tag, etc., can be manufactured. Furthermore, the organic transistor can be used as a sensor because the organic transistor changes the characteristics thereof due to external stimuli such as a chemical compound.

Hereinafter, the present invention is explained in more detail with giving the Examples, but the present invention is not limited thereto. In the Examples, "part(s)" represents part(s) by mass, and "%" represents % by mass (mass %), respectively, unless otherwise specified.

Example 1 (Production of Composition of the Present Invention, Organic Thin Film Formation Material Including the Composition and Organic Thin Film Obtained by Using the Formation Material)

Specific compounds No. 1 and No. 3 shown above were dissolved at a mass ratio of No. 1:No. 3=9:1 in chlorobenzene so as for the total concentration of the compounds to be 0.1%. This solution was dropped on a silicon substrate having a silicon oxide film with a thickness of 100 nm, blade coated at a speed of 2.5 μm/sec using a glass blade, and then dried at 70° C. The thickness of the obtained organic thin film was about 9 nm, which was a homogeneous and had no crack over a large area as shown by the polarizing microscope image of FIG. 3 (In the figure, the arrow indicates the sweep direction of the glass blade and the area between the dotted lines is an area which the film was formed effectively by the method described in this Example.).

Example 2 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 and No. 3 shown above were dissolved at a mass ratio of No. 1:No. 3=5:5 in chlorobenzene so as for the total concentration of the compound to be 0.1%. The obtained organic thin film was homogeneous and had no crack over a large area as shown by the polarizing microscope image of FIG. 4.

Example 3 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 and No. 3 shown above were dissolved at the mass ratio of No. 1:No. 3=3:7 in chlorobenzene so as for the total concentration of the compound to be 0.1%. The film thickness of the obtained organic thin film was between 9 and 18 nm, and the thin film was homogeneous and had no crack over a large area as shown by the polarizing microscope image of FIG. 5.

Example 4 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 and No. 3 shown above were dissolved at the mass ratio of No. 1:No. 3=97:3 in chlorobenzene so as for the total concentration of the compound to be 0.1%. The thickness of the obtained organic thin film was between 4 and 9 nm, and the thin film was homogeneous and had no crack over a large area as shown by the polarizing microscope image of FIG. 6.

Example 5 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 and No. 3 shown above were dissolved at the mass ratio of No. 1:No. 3=1:9 in chlorobenzene so as for the total concentration of the compound to be 0.1%. The obtained organic thin film had no crack, but multiple domains were piled up as shown by the polarizing microscope image of FIG. 7.

Example 6 (Production of Composition of the Present Invention, Organic Thin Film Formation Material Including the Composition and Organic Thin Film Obtained by Using the Formation Material)

The organic thin film was prepared in the same method as Example 1, except that specific compounds No. 2 and No. 3 were dissolved at the mass ratio of No. 2:No. 3=8:2 in chlorobenzene so as for the total concentration of the compounds to be 0.1%. The obtained organic thin film was homogeneous and had no crack over a large area as shown by the polarizing microscope image of FIG. 8.

Example 7 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 and No. 3 shown above were dissolved at the mass ratio of No. 1:No. 3=40:60 in chlorobenzene so as for the total concentration of the compound to be 0.1%. The obtained organic thin film was homogeneous and had no crack over a large area as shown by the polarizing microscope image of FIG. 9.

Example 8 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 shown above and No. 24 shown below were dissolved at the mass ratio of No. 1:No. 24=50:50 in chlorobenzene so as for the total concentration of the compound to be 0.1%. The obtained organic thin film was homogeneous and had no crack over a large area as shown by the polarizing microscope image of FIG. 10.

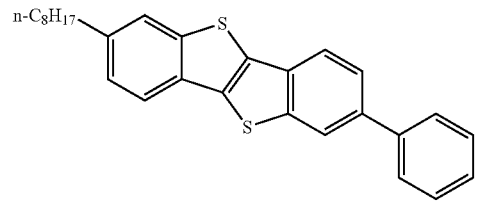

No.24(22)

Example 9 (Production of Composition of the Present Invention, Organic Thin Film Formation Material Including the Composition and Organic Thin Film Obtained by Using the Formation Material)

The organic thin film was prepared in the same method as Example 1, except that specific compounds No. 3 and No. 5 shown above were dissolved at the mass ratio of No. 3:No. 5=50:50 in chlorobenzene so as for the total concentration of the compound to be 0.1%. The obtained thin film was homogeneous and had no crack over a large area as shown by the polarizing microscope image of FIG. 11.

Example 10 (Production of Composition of the Present Invention, Organic Thin Film Formation Material Including the Composition and Organic Thin Film Obtained by Using the Formation Material)

The organic thin film was prepared in the same method as Example 1, except that specific compounds No. 1 and No. 5 shown above were dissolved at the mass ratio of No. 1:No. 5=50:50 in chlorobenzene so as for the total concentration of the compounds to be 0.1%. The obtained organic thin film was homogeneous and had no crack over a large area was obtained as shown by the polarizing microscope image of FIG. 12.

Example 11 (Production of Composition of the Present Invention, Organic Thin Film Formation Material Including the Composition and Organic Thin Film Obtained by Using the Formation Material)

The organic thin film was prepared in the same method as Example 1, except that specific compounds No. 15 and No. 16 shown above were dissolved at the mass ratio of No. 15:No. 16=50:50 in chlorobenzene so as for the total concentration of the compounds to be 0.1%. The obtained organic thin film was homogeneous and had no crack over a large area as shown by the polarizing microscope image of FIG. 13.

Comparative Example 1 (Production of Comparative Composition, Organic Thin Film Formation Material Including the Composition and Organic Thin Film Obtained by Using the Formation Material)

The organic thin film was prepared in the same method as Example 1, except that only specific compound No. 1 shown above was dissolved in chlorobenzene so as for the concentration of the compound to be 0.1%. The obtained organic thin film was inhomogeneous and had cracks partially as shown by the polarizing microscope image of FIG. 14.

Comparative Example 2 (Production of Comparative Composition, Organic Thin Film Formation Material Including the Composition and Organic Thin Film Obtained by Using the Formation Material)

The organic thin film was prepared in the same method as Example 1, except that only specific compound No. 2 shown above was dissolved in chlorobenzene so as for the concentration of the compound to be 0.1%. The obtained organic thin film was inhomogeneous and had cracks partially as shown by the polarizing microscope image of FIG. 15.

Example 12 (Production and Evaluation of Organic Thin Film Transistor Including Organic Thin Film of the Present Invention)

A source and a drain electrode was formed by vacuum evaporation of gold on the organic thin film formed in Example 1 by using a shadow mask to produce the organic thin film transistor device composed of 25 elements. This device has four types of channel lengths (50, 100, 200 and 250 μm), and each of the devices has a channel width of 350 μm. The organic transistor device produced in this manner was a top contact type and FIG. 1B shows the structure thereof. As for the organic transistor device of this Example, the thermally oxidized film in the n-doped silicon wafer having a thermal oxide film of 100 nm (relative dielectric constant of 3.9) has functions of an insulating layer (4), and the n-doped silicon wafer has both functions of the substrate (6) and the gate electrode (5).

Carrier mobility depends on the amount of current which was flowed when an electric voltage is applied between source and domain under the conditions that an electric voltage is applied to the gate. By measuring this current value, mobility which is the characteristic of the transistor can be determined. The mobility is able to be calculated from the equation (a) expressing the electrical characteristics of carrier species generated in the organic semiconductor layer, as a result of applying gate electrolysis to $SiO_2$ as an insulator.

$$Id = Z\mu Ci(Vg-Vt)^2/2L \quad (a)$$

Here, Id is a saturated source drain current value, Z is a channel width, Ci is an electric capacity of insulator, Vg is a gate potential, Vt is a threshold electric potential, L is a channel length, and μ is a mobility ($cm^2/V \cdot s$) which is to be calculated. Ci is a dielectric constant of a $SiO_2$ insulating film used, Z and L depend on a device structure of an organic transistor device, Id and Vg is fixed at the time of measuring a current value of an organic thin film transistor device, and Vt is able to be calculated from Id and Vg. The mobility at each gate potential is able to be calculated by assigning each value to the equation (a).

Current-voltage characteristics of the formed organic thin film transistor device were measured under the conditions of sweeping a Vg from 0 V to −50 V and at Vd=−50 V. All of the 25 elements were driven, and the mobilities calculated from the above equation were up to 6.8 $cm^2/V \cdot s$, and all of the mobilities of 25 elements were 1 or more.

Example 13 (Production and Evaluation of Organic Thin Film Transistor Including Organic Thin Film of the Present Invention)

A top contact type organic transistor device composed of 40 elements was formed in the same method as in Example 12, except that a step of forming a film of 2,3,5,6-tetrafluoro-7,7,8,8-tetracyano quinodimethane was conducted for the purpose of decreasing damage on the organic thin film as a pretreatment of the step of forming a film by vacuum evaporation of gold (the formation of the source drain electrode) in the method of forming the organic thin film transistor in Example 12. The channel length and the channel width in this Example are 200 μm and 500 μm, respectively. Current-voltage measurement was conducted by the same method as in Example 12. All of 40 elements were driven, and the mobilities calculated from the above equation were up to 8.8 $cm^2/V \cdot s$, and all of the mobilities of 40 elements were 1 or more.

Comparative Example 3 (Production and Evaluation of Organic Thin Film Transistor Including Comparative Organic Thin Film)

A top contact type organic transistor was formed in the same method as in Example 12, except that the organic thin film formed in Example 2 was replaced with the organic thin film formed in Comparative Example 1. In the results of the current-voltage measurement which was conducted by the same method as in Example 12, all of 20 elements were driven, and some of the mobilities calculated from the results of the measurement was up to 8.4 $cm^2/V \cdot s$, however the mobility of the place where defects existed was 0.019 $cm^2/V \cdot s$ and large unevenness was found.

Comparative Example 4 (Production and Evaluation of Organic Thin Film Transistor Including Comparative Organic Thin Film)

A top contact type organic transistor was formed by the same method as in Example 12, except that the organic thin film formed in Example 2 was replaced with the organic thin film formed in Comparative Example 2. From the results of current-voltage measurement which was conducted by the same method as in Example 12, some of the mobilities calculated from the results of measurement were up to 5.2 $cm^2/V \cdot s$, however only 13 out of 31 elements were driven and large unevenness was found.

As a characteristic of the practical organic thin film, transistor elements formed on the same substrate are required to show uniformly high mobility (higher mobility is better) with no variability. Therefore, the yields were calculated from the following formula to summarize the evaluation results of the above Examples and Comparative Examples in Table 1.

Yield (%)=(The number of elements having a mobility of 1 $cm^2/V \cdot s$ or more)/(the number of all elements formed on the same substrate)×100

TABLE 1

| Characteristic evaluation of transistor | Organic thin film constituting transistor | Film conditions | Maximum mobility ($cm^2/V \cdot s$) | Yield (number of all elements) |
|---|---|---|---|---|
| Example 12 | Example 1 | no crack and evenness | 6.8 | 100% (25) |
| Example 13 | Example 1 | no crack and evenness | 8.8 | 100% (40) |
| Comparative Example 3 | Comparative Example 1 | cracked and unevenness | 8.4 | 70% (20) |
| Comparative Example 4 | Comparative Example 2 | cracked and unevenness | 5.2 | 35% (31) |

In the organic thin film transistor including the organic thin film obtained by using the semiconductor composition of the present invention as an organic semiconductor layer, the yield of the practical elements showing high mobility is 100% and the results indicate uniformly high mobilities. On the other hand, in Comparative Example 3 and Comparative Example 4 using the semiconductor component which is a single component, some elements showed maximum mobilities which are about the same level as Example 12 and Example 13, however, many elements which drive defectively or whose mobility is lower than 0.1 cm$^2$/V·s were found. The yields calculated from the above equation were 70% and 35%, respectively, and the results did not show uniformly high mobility without variation. The low molecule compound used in Comparative Example 4 was described, for example, in WO2014/038708 as a compound having low variation of mobilities. However, the evaluation of variation in WO2014/038708 was conducted by measuring and comparing 5 elements and it is silent about variation of the practical elements as in the present Examples. In Comparative Example 4, 31 elements were formed on the same substrate and then measured, however the yield of the compound used as a single component was low. From the above, the composition of the present invention is excellent in the properties which are suitable for practical use to the know compounds.

Usability for Industry

As described above, the composition of present invention and the organic thin films including the composition can form a thin film which is homogeneous over a large area and can be used in the fields of organic semiconductor devices, etc., including organic transistor devices.

The same names are given the same numbers in FIG. 1 and FIG. 2.

1 Source electrode
2 Semiconductor layer
3 Drain electrode
4 Insulating layer
5 Gate electrode
6 Substrate
7 Protective layer

The invention claimed is:

1. A composition comprising two thienothiophene compounds, wherein
both thienothiophene compounds are represented by formula (1) or
both thienothiophene compounds are represented by formula (3):

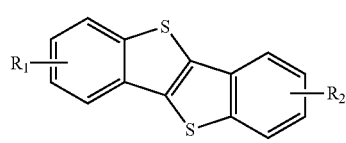

(1)

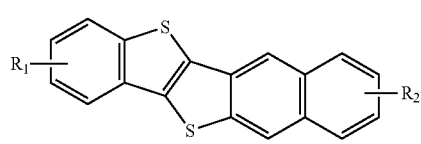

(3)

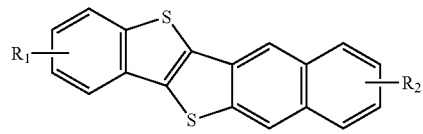

(3)

wherein in formulas (1) and (3), either one of $R_1$ and $R_2$ represents an alkyl group, and the other represents an aromatic hydrocarbon group or a substitution represented by formula (5):

(5)

wherein in formula (5), $R_3$ represents an aromatic hydrocarbon group,
wherein when
one of the thienothiophene compounds is a compound represented by formula (1) and either one of $R_1$ and $R_2$ represents an aromatic hydrocarbon and
the other thienothiophene compound is a compound represented by formula (1) and either one of $R_1$ and $R_2$ represents the substitution represented by formula (5), the alkyl groups represented by $R_1$ or $R_2$ in the two thienothiophene compounds are independently n-hexyl group, n-octyl group, or n-decyl group.

2. The composition according to claim 1,
wherein the two thienothiophene compounds have different minimum carbon chain numbers,
the minimum carbon chain numbers being defined as a minimum number of carbons sequentially bonded through direct bonds between carbon atoms from a terminal carbon atom of $R_1$ to a terminal carbon atom of $R_2$,
where
when $R_1$ or $R_2$ represents the alkyl group, the terminal carbon atom is a terminal carbon atom of a main chain of the alkyl group;
and
when $R_1$ or $R_2$ represents the aromatic hydrocarbon group or the heterocyclic group, the terminal carbon atom is a carbon atom on $R_1$ or $R_2$ farthest from a carbon atom which $R_1$ or $R_2$ attaches to, on the benzothiophene ring or the naphtothiophene ring.

3. The composition according to claim 2, wherein the difference between the minimum carbon chain numbers of the two thienothiophene compounds is 2 or more and 18 or less.

4. The composition according to claim 3, wherein the difference between the minimum carbon chain numbers of the two thienothiophene compounds is 2 or more and 12 or less.

5. The composition according to claim 1, wherein either one of the two thienothiophene compounds is represented by any one of formulas (6) and (8):

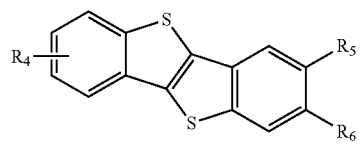

(6)

-continued

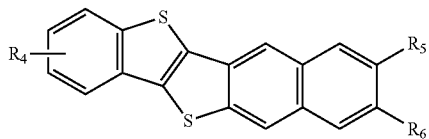
(8)

wherein in formulas (6) and (8), $R_4$ represents an alkyl group, and either one of $R_5$ and $R_6$ represents a hydrogen atom and the other represents an aromatic hydrocarbon group.

6. The composition according to claim 1, comprising the two thienothiophene compounds having different carbon numbers of a main chain of the alkyl group in the alkyl group which either one of the substituent $R_1$ or $R_2$ represents, wherein the content ratio of the thienothiophene compound having a main chain having a larger carbon number is 1 mass % or more and 90 mass % or less.

7. The composition according to claim 6, comprising the two thienothiophene compounds, wherein a difference of the carbon number of the main chain of the alkyl group which either one of the substituent $R_1$ or $R_2$ represents is 2 or more and 8 or less.

8. The composition according to claim 1, wherein at least one of the two thienothiophene compounds is a thienothiophene compound represented by any one of formulas (10) and (12):

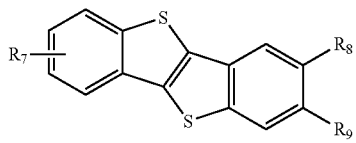
(10)

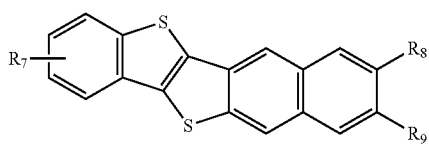
(12)

wherein in formulas (10) and (12), $R_7$ represents an alkyl group, either one of $R_8$ and $R_9$ represents a hydrogen atom, and the other represents a substituent group represented by formula (5).

9. The composition according to claim 1, wherein either one of the thienothiophene compounds is a thienothiophene compound represented by any one of formulas (6) and (8):

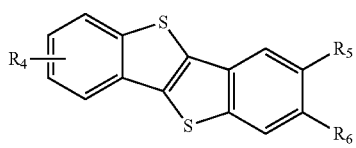
(6)

-continued

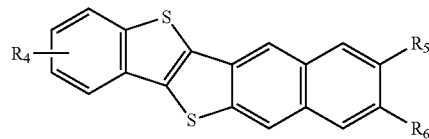
(8)

wherein in formulas (6) and (8, $R_4$ represents an alkyl group, either one of $R_5$ and $R_6$ represents a hydrogen atom, and the other represents an aromatic hydrocarbon group, and the other is a thienothiophene compound represented by any one of formulas (10) and (12):

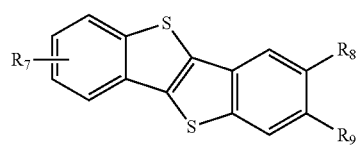
(10)

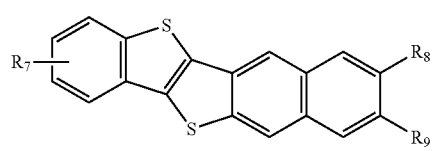
(12)

wherein in formulas (10) and (12), $R_7$ represents an alkyl group, either one of $R_8$ and $R_9$ represents a hydrogen atom, and the other represents a substituent group represented by formula (5).

10. The composition according to claim 9, wherein a content of the thienothiophene compound represented by any one of formulas (10) and (12) to a total mass of the two thienothiophene compounds is from 5 to 40 mass %.

11. An organic thin film formation material comprising the composition according to claim 1 and an organic solvent.

12. An organic thin film obtained by using the organic thin film formation material according to claim 11.

13. The organic thin film according to claim 12, having a thickness of 4 nm or more and 30 nm or less.

14. A method for producing an organic thin film comprising:
applying or printing the organic thin film formation material according to claim 11 to a substrate, and
removing the organic solvent from the organic thin film formation material applied or printed to the substrate.

15. An organic semiconductor device comprising the organic thin film according to claim 12.

16. The organic semiconductor device according to claim 15, wherein the organic semiconductor device is an organic thin film transistor.

17. The composition according to claim 1, wherein either one of $R_1$ and $R_2$ represents an alkyl group having a carbon number of 6 to 14.

18. The composition according to claim 17, wherein either one of $R_1$ and $R_2$ represents a phenyl group.

* * * * *